(12) United States Patent
Harker

(10) Patent No.: US 7,840,300 B2
(45) Date of Patent: Nov. 23, 2010

(54) FULL SPECTRUM LAPIDARY 3D IMAGE SCANNER AND METHOD

(76) Inventor: Robert Arthur Harker, 4710 NW. 18th Pl., Gainesville, FL (US) 32605

( * ) Notice: Subject to any disclaimer, the term of this patent is extended or adjusted under 35 U.S.C. 154(b) by 814 days.

(21) Appl. No.: 11/809,661

(22) Filed: May 31, 2007

(65) Prior Publication Data

US 2008/0067382 A1   Mar. 20, 2008

Related U.S. Application Data

(60) Provisional application No. 60/809,484, filed on May 31, 2006.

(51) Int. Cl.
*G06F 19/00* (2006.01)
(52) U.S. Cl. .................. 700/112; 700/114; 700/195
(58) Field of Classification Search .............. None
See application file for complete search history.

(56) References Cited

U.S. PATENT DOCUMENTS

| 3,650,018 | A | * | 3/1972 | Perry et al. | 408/35 |
| 3,828,758 | A | * | 8/1974 | Cary | 125/13.01 |
| 3,921,342 | A | * | 11/1975 | Day | 451/550 |
| 4,043,080 | A | * | 8/1977 | Maxwell | 451/123 |
| 5,621,648 | A | * | 4/1997 | Crump | 700/112 |
| 5,687,251 | A | * | 11/1997 | Erler et al. | 382/133 |
| 5,880,961 | A | * | 3/1999 | Crump | 700/112 |
| 6,074,283 | A | * | 6/2000 | Maeda et al. | 451/53 |
| 6,091,999 | A | * | 7/2000 | Crump et al. | 700/112 |
| 7,565,084 | B1 | * | 7/2009 | Wach | 398/201 |
| 2003/0162226 | A1 | * | 8/2003 | Cima et al. | 435/7.1 |
| 2004/0043709 | A1 | * | 3/2004 | Heimes et al. | 451/41 |
| 2004/0106358 | A1 | * | 6/2004 | Tsao et al. | 451/8 |
| 2004/0235406 | A1 | * | 11/2004 | Duescher | 451/527 |
| 2005/0202660 | A1 | * | 9/2005 | Cohen et al. | 438/533 |
| 2006/0257286 | A1 | * | 11/2006 | Adams | 422/82.01 |

OTHER PUBLICATIONS

Beck, J.D., et al., "Three-Dimensional Imaging of Trabecular Bone Using the Computer Numerically Controlled Milling Technique", *Bone*, Sep. 1997, pp. 281-287, vol. 21, No. 3, Elsevier Science, Inc.
Sinha, G., "Secrets of the Very Small: A New Microscope Enables Scientists to See the Intricate 3-D Structure of Everything from Cartilage to Velcro", *Popular Science*, Dec. 2001, pp. 80-83.

* cited by examiner

*Primary Examiner*—Bernard E Souw
*Assistant Examiner*—Andrew Smyth
(74) *Attorney, Agent, or Firm*—Saliwanchik, Lloyd & Saliwanchik

(57) ABSTRACT

The subject invention pertains to an apparatus and method for collecting 2-D data slices of a specimen. Embodiments can incorporate a lapidary platen and an image recording system to image a specimen. The lapidary wheel platen can provide an imaging plane such that an image can be taken as the lapidary wheel platen abrades a surface of the specimen. A specimen mount can maintain the surface of the specimen properly aligned in the image plane. The imaging system can be a continuous recording system such as a video camera, a discrete recording system such as a flatbed scanner, or combinations of continuous and discrete recording systems to simultaneously collect two distinct data sets. The 2-D data set(s) can then be processed to create intricate 3-D color models.

50 Claims, 21 Drawing Sheets

FULL SPECTRUM LAPIDARY 3D IMAGE SCANNER AND METHOD

CROSS-REFERENCE TO RELATED APPLICATION

The present application claims the benefit of U.S. Application Ser. No. 60/809,484, filed May 31, 2006, which is hereby incorporated by reference herein in its entirety, including any figures, tables, or drawings.

BACKGROUND OF INVENTION

There are three general methods currently being used to collect data for forming 3-D images of the internal structure of a specimen. The first method involves hand registering sliced specimens, which are cut using a microtome, mounted on a slide, and individually photographed. As each slice of specimen must be mounted and photographed, consistent alignment of the photographs can be difficult to obtain.

The second method involves Computed Numerically Controlled (CNC) milling machining of a specimen, imaging of the exposed cross-section with a camera, and processing the images. An article by Beck, Canfield, Haddock, Chen, Kothari, and Keaveny, titled "Three-dimensional imaging of trabecular bone using the Computer Numerically Controlled Milling Technique", discloses a method where thin layers are serially removed from an embedded bone specimen by using a CNC machine and each exposed cross section is imaged using a digital camera. The precise positioning of the specimen under the camera is achieved by using the programmable feature of the CNC milling machine.

Both the microtome lab method and the CNC machining method rely on cutting portions of a specimen with cutting tools. However, these cutting tools require sharpening and/or replacement in order to maintain their effectiveness.

The third method utilizes various non-destructive systems such as CT, MRI, PET, NMR, and X-ray. Non-destructive systems such as CT, MRI, PET, NMR, and X-ray lack the ability to directly capture internal chemical or physical properties and structure. In particular, these non-destructive systems are unable to capture true internal color or direct spectroscopic data.

Accordingly, there is a need for an easily alignable method and system for direct capture of true internal chemical and/or physical properties of a specimen.

BRIEF SUMMARY

The subject invention pertains to an apparatus and method for collecting 2-D data slices of a specimen. Embodiments can incorporate a lapidary platen and an image recording system to image a specimen. The lapidary wheel platen can provide an imaging plane such that an image can be taken as the lapidary wheel platen abrades a surface of the specimen. A specimen mount can maintain the surface of the specimen properly aligned in the image plane. The imaging system can be a continuous recording system such as a video camera, a discrete recording system such as a flatbed scanner, or combinations of continuous and discrete recording systems to simultaneously collect two distinct data sets. The 2-D data set(s) can then be processed to create intricate 3-D color models.

BRIEF DESCRIPTION OF DRAWINGS

FIG. 2A shows a fish specimen prepared for processing, and FIG. 2B shows a sample advance/shuttle retract mechanism.

FIG. 5A shows the motor mount and camera port (inside), and FIG. 5B shows the servo motor, camera port and LED light array.

FIG. 12A shows an assembled integrated pressurized sample advance mechanism with LVDT depth sensor, and FIGS. 12B and 12C show a sample pressure line, LVDT tubing connector and base, LVDT sensor body and clamp, LVDT sensor shuttle, sample holder cap, sample plunger, and sample holder body.

DETAILED DISCLOSURE

Figure 1:
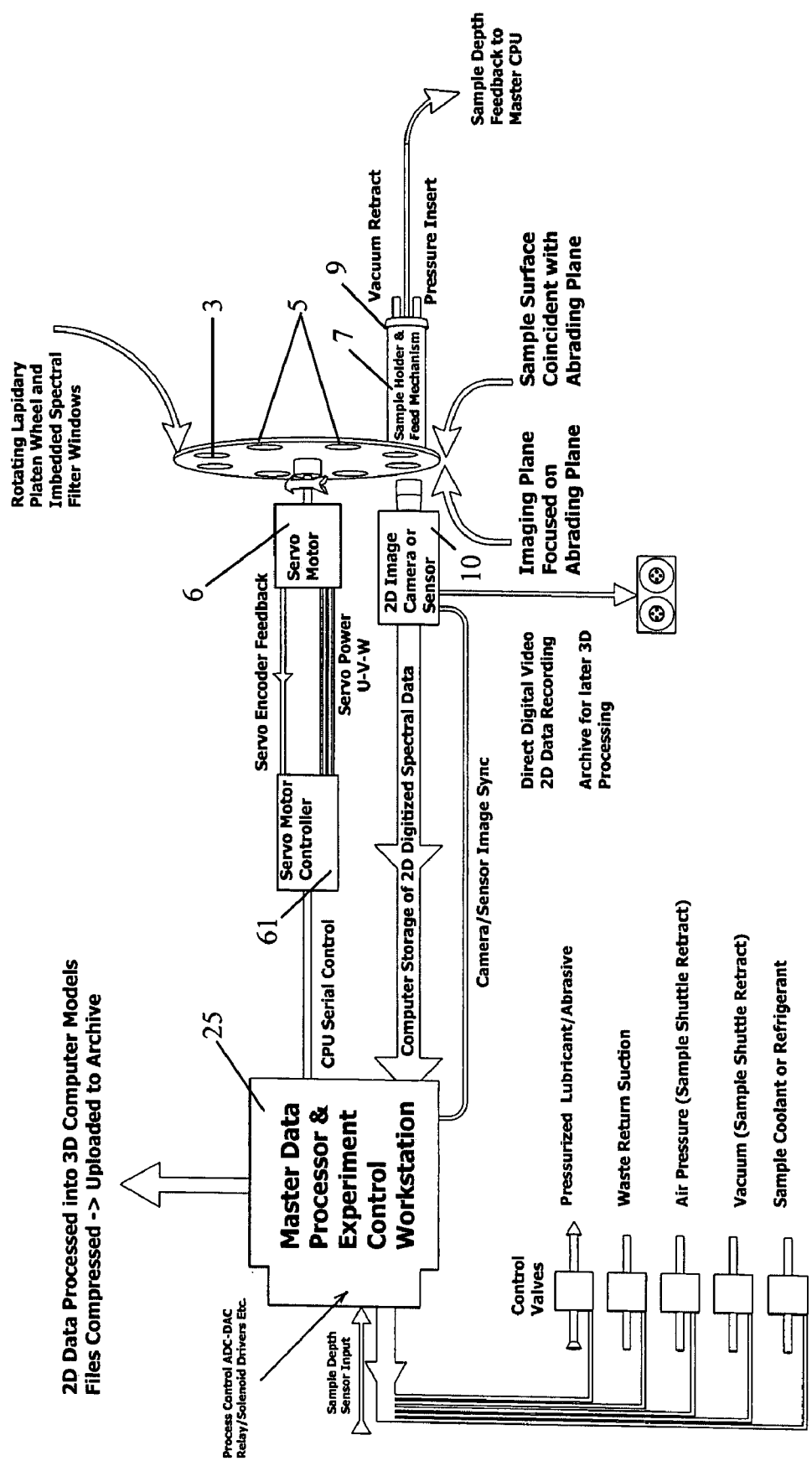
FIG. 1 shows a schematic of a 3D lapidary scanner in accordance with an embodiment of the subject invention.

The subject invention pertains to an apparatus and method for capturing 3-D tomographically registered full spectrum computer digitized images of internal structures of specimens. In particular, the subject apparatus and method can collect 2-D data slices, which can be processed to create intricate 3-D models. Embodiments of the subject invention can provide naturally registered and aligned datasets with detail that can reveal structure preferably in the 100 micron scale, more preferably in the 1 micron scale, and even more preferably in the 100 nanometer scale. In a specific embodiment, the 2-D data slices can be used to provide full color 3-D models.

In an embodiment, 2-D data slices can be obtained using a lapidary system to remove layers of specimen. In a specific embodiment, a lapping wheel platen, which incorporates a spinning clear surface, can be used to remove layers of specimen such that the surface of the lapping wheel platen is clear where abrading or cutting surface is in an imaging plane. An imaging system can be mounted to the lapidary system to record images as the layers of specimen are removed.

Embodiments of the invention can utilize a variety of techniques for acquiring images of the specimen in the image plane. In specific embodiments, the image data sets can be collected by, for example, focused plane imaging or contact image sensing using many available sensors. Sensing instruments can be applied to either the focal or contact image plane because the exposed polished surface remains fixed. Contact image sensors may be conveniently integrated into the lapidary platen or fixed on a window or opening in the platen. Examples of sensors that can be incorporated with embodiments of the subject system include, but are not limited to, one or more of the following: full spectrum light detectors, such as standard photographic emulsions, photomultipliers, charged couple devices (CCD), photocells, photo-resistors, complementary metal oxide semiconductor (CMOS) detectors, and hybrid integrated circuits; electromagnetic detectors such as antennas, coils, RF energy detectors, and triboelectrical effect sensors; physical property detectors such as thermocouples, resistance temperature detectors, pH-sensors, blackbody thermometer, and hall effect sensors; general scientific sensing instruments such as HPLC, scanning probe microscopes (SPM), scanning electron microscopes (SEM), and electron microscopes; and medical sensing instrumentation such as protein and peptide sensors, lipid sensors, hormone sensors, toxin sensors, and neurotransmitter sensors.

One or more sensors may be employed concurrently or form a hybrid detector to scan a specimen to produce multiple tomographic data sets that are concentric to one another. For example, an image can be collected by a sensor sensitive to neuropeptides and another image can be collected by a sensor sensitive to calcium, and then one model can show bone and the other model can show nerves, or a combined model can show both bone and nerve.

Although the lapidary system described below incorporates a rotary lapidary wheel platen, alternative embodiments can be used. In one alternative embodiment, the lapidary platen can take the form of an orbital sander configuration. In another alternative embodiment, the lapidary platen can take the form of an infinite loop belt. In yet another alternative embodiment, the lapidary platen can take the form of a reciprocating surface.

In particular, performing lapidary or direct abrasion methods can expose new structures on a plane that can be made coincident to the optical imaging plane of an image-recording device or photographic camera positioned to record the images as the layers are removed. Capturing an image of each exposed layer image offers the ability to later recombine these images into 3-D representations of the artifact, creature, biologic, or material sample. In an embodiment, 3-D representations can be achieved through standard cinema or digital imaging methods. In accordance with the embodiments of the subject method, the entire sample undergoing imaging is sacrificed by the lapidary or abrasion process.

In a specific embodiment, the subject apparatus can incorporate a lapidary system, an imaging system, and a control system. FIG. 1 shows a schematic of an embodiment having a lapidary system, an imaging system, and a control system. Referring to the schematic shown in FIG. 1, a master data processor 25 can control a lapidary scanner. The master data processor 25 can coordinate the rotation of a rotating lapidary platen 3 and storage of the captured data from one or more image capture mechanisms 10. A sample feed 9 can abut the rotating lapidary platen 3 such that a sample's surface is coincident with the abrading plane. The rotating lapidary platen 3 has embedded opaque filters 5 that form an abrading plane. An image capture device 10 can be used to provide 2D digitized data of the sample 7. A direct digital video capture device can be used as the image capture device. Alternatively, or in addition to a direct video capture device, a discrete image capture device can be utilized as the image capture device 10. The image plane of the image capture device 10 can be focused on the abrading plane. In one embodiment, a servo motor 6 can be used to rotate the lapidary platen 3.

Figure 2A:
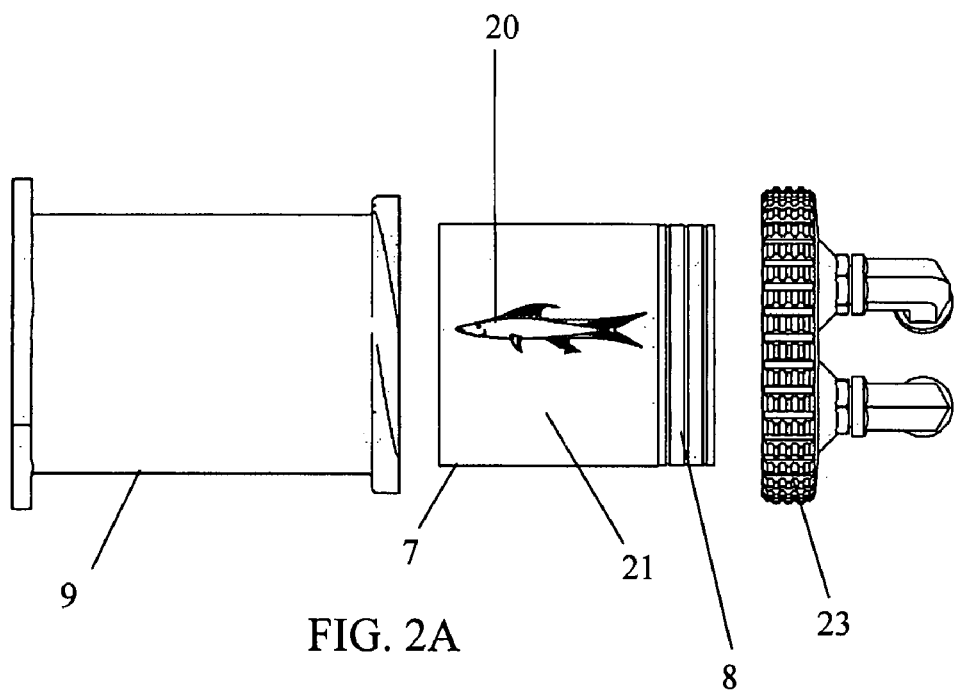
FIGS. 2A and 2B show an embodiment of a sample shuttle mechanism in accordance with an embodiment of the subject invention, where
Figure 2B:
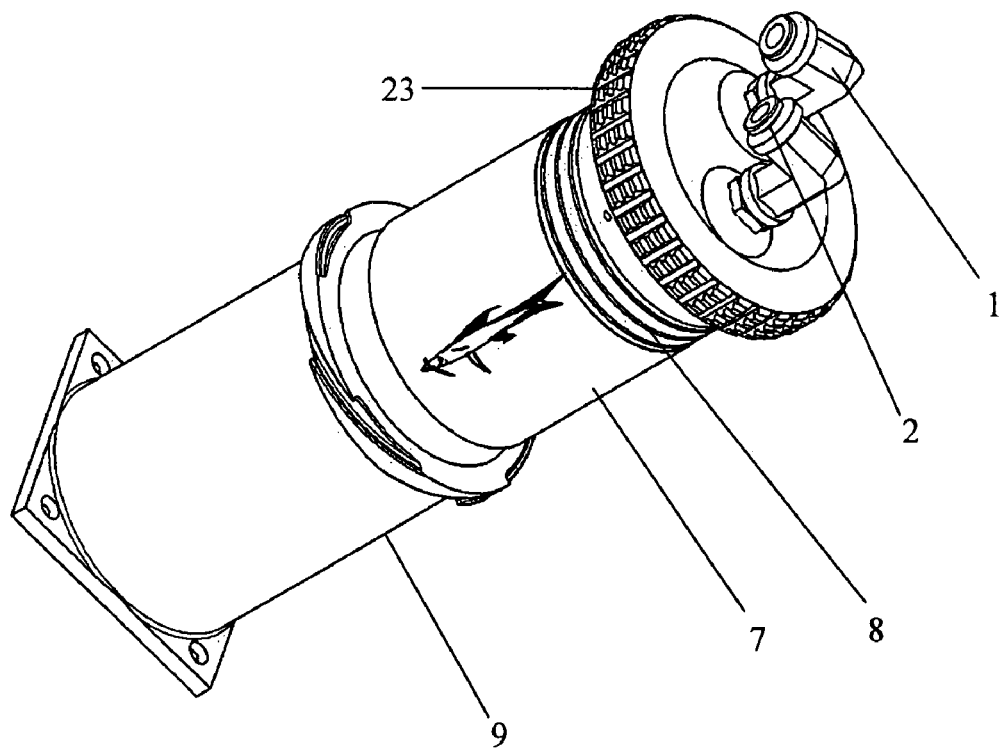

The master data processor 25 can also control pressurized lubricant and/or abrasive for the lapidary platen, waste return suction, air pressure and vacuum for a sample shuttle insert in the sample feed 9, and sample coolant. FIGS. 2A and 2B show a specific embodiment of a sample holder and feed mechanism. The vacuum control 1 and pressure control 2 for the sample shuttle in the sample feed can control the position of the sample. The pressure caused by the pressure control 2 can cause the sample shuttle 8 to insert deeper into the sample feed 9 and maintain the sample 7 against the rotating lapidary platen 3. The vacuum caused by the vacuum control 1 can cause the sample shuttle 8 to retract away from the rotating lapidary platen 3.

In an embodiment, the lapidary system component can incorporate a sample mount, lapidary platen, and driving mechanism. In an embodiment, the specimen can be prepared for mounting to the lapidary system. For example, a specimen can be cast and mounted in a rigid compound. In a specific embodiment, by use of specialized mounting systems and methods, dried or frozen specimens can be cast into rigid optical or opaque mounting compounds in specialized lapidary sample mounts. A special sacrificial mold material can be used to cast and mount each specimen in rigid compounds that hold specimens during mechanical layer abrasion operations. The compounds can be chosen for their optical and their other physical properties. In an embodiment, high contrast mounting materials, dye compounds, and/or tagants can be used to enhance or attenuate the display of organic and other structures within the specimen. In one embodiment, a void within a specimen can be perforated and injected with contrast mount material before casting into the rigid compound.

FIGS. 2A and 2B show an example of a prepared specimen for use with the subject lapidary system. In this example, a fish specimen 20 is cast and mounted in a rigid compound 21. In an embodiment, the prepared specimen 7 can be positioned within a sample feed 9 and shuttle mechanism 8 for advancing and retracting the sample.

The mounted specimen can be held in a rigid position in regard to an x-y plane and can be moved, or allowed to move, toward the optical plane (in the z-direction) as each layer is exposed such that the new exposed layer is always in contact with the imaging plane. Alternatively, the specimen can be held rigid as the lapidary platen can be brought toward the specimen as each layer of the specimen is exposed.

In an embodiment where the surface of the cut represents an x-y plane and the depth of cut is along a-z axis, a sample mount can directly support samples from moving along the z-axis by direct force contact. This z-axis control can provide flexibility and control of the depth of cut.

In operation, referring to FIG. 2B, for an embodiment incorporating a sample shuttle mechanism for advancing and retracting the sample along the z-axis, a cap 23 can have a vacuum port 1 and a pressure port 2. Increasing the air pressure through the pressure port 2 can cause the sample shuttle to move the sample toward the lapidary wheel platen 3. Reducing the pressure through the vacuum port 1 can cause the sample shuttle to retract the sample away from the lapidary wheel.

In an embodiment, the depth of cut or rate of cut into a sample can be estimated by determining a gross measurement of the length of a sample before mounting and applying the gross measurement to the model data after processing. Specifically, slice registrations in the z-axis can be estimated over the entire distance of the sample cut in the z-axis. For an example where 500,000 rotations can occur per centimeter of sample, the estimated depth of cut can be estimated at 20 nm/rotation.

Figure 12A:
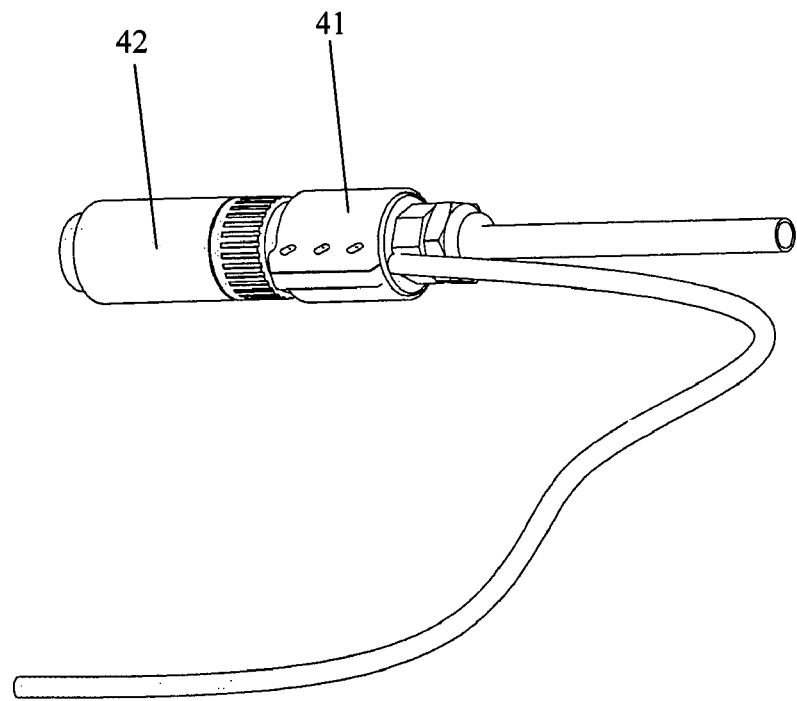
FIGS. 12A-12C show an embodiment of a sample shuttle mechanism incorporating a LVDT depth sensor in accordance with an embodiment of the subject invention, where
Figure 12B:
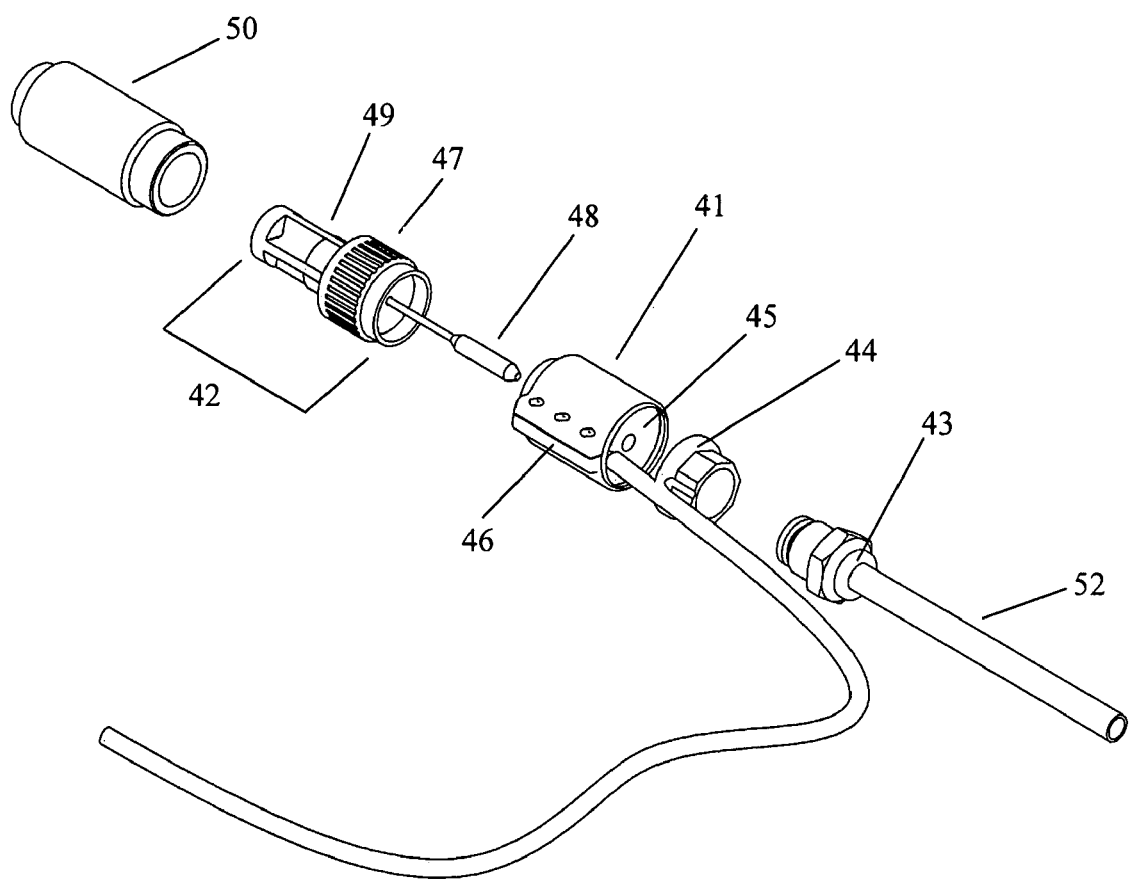
Figure 12C:
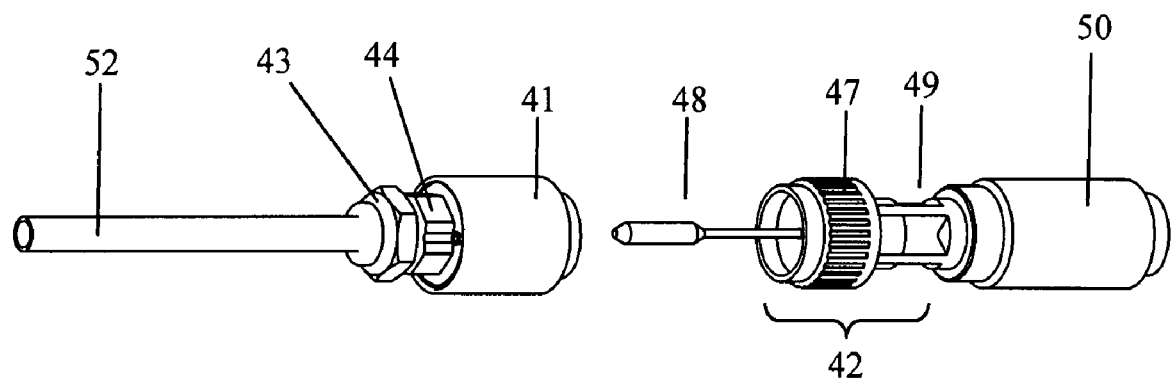

In another embodiment, the sample shuttle can incorporate a mechanism for determining the depth of a cut or rate of cut into a sample. Such a mechanism for determining the depth of a cut or rate of cut into a sample can be, for example, a direct electronic depth sensor or a mechanical machine tool such as a micrometer. In one embodiment, a Linear Velocity Displacement Transducer (LVDT) can be fixed to the sample shuttle. Referring to FIGS. 12A-12C, an LVDT sensor 41 can be attached to the shuttle 42 holding the sample. In an embodiment, the LVDT sensor 41 can be part of an LVDT assembly. In particular, a tubing connector 43 can be threaded into the base 44 of the LVDT. In one embodiment, the base 44 of the LVDT can be bonded and potted into the LVDT sensor body 45. The sensor body can incorporate a clamp 46, which can be threaded into a sample holder cap 47. A sealant, for example an RTV sealant, can also be used to keep the clamp 46 within the holder cap 47. In a further embodiment, the sensor clamp 46 can have three screws (not shown) to adjust the position of the LVDT. A sensor shuttle 48 can be threaded through the sample holder cap 47 and into the sample plunger 49. The sensor shuttle can be fed through the tubing connector 43 and the sensor body 45 before being threaded into the sample plunger 49. In this way, the LVDT assembly 40 can be incorporated into the sample holder cap 47 and in turn be incorporated into the sample shuttle mechanism 42. For operation, a pressure line 52 can be connected to the tubing connector 43. The pressure line 52 can be used to control the movement of the plunger 49, which moves both the sample and the LVDT shuttle 48, which is attached to the plunger 49. A new sample can be inserted into the sample holder 50 by unscrewing the cap 47.

In an embodiment, the LVDT sensor 41 can provide measurements, for example, to the μm range. Estimates to the nm range can be derived through the full model after processing. For example, where 500 rotations provides a reading of 25 μm from the LVDT sensor, the estimated depth of a cut can be estimated at 50 nm/rotation.

In yet another embodiment, disposable wear gauges can be imbedded into the mounting compound. These disposable gauges can indicate when certain depths are reached. In an embodiment, the estimated depth of a cut caused by one rotation of the lapidary wheel platen can be calculated from the number of rotations necessary to abrade the sample to the depths indicated by one or more of the disposable wear gauges.

Figure 3A:
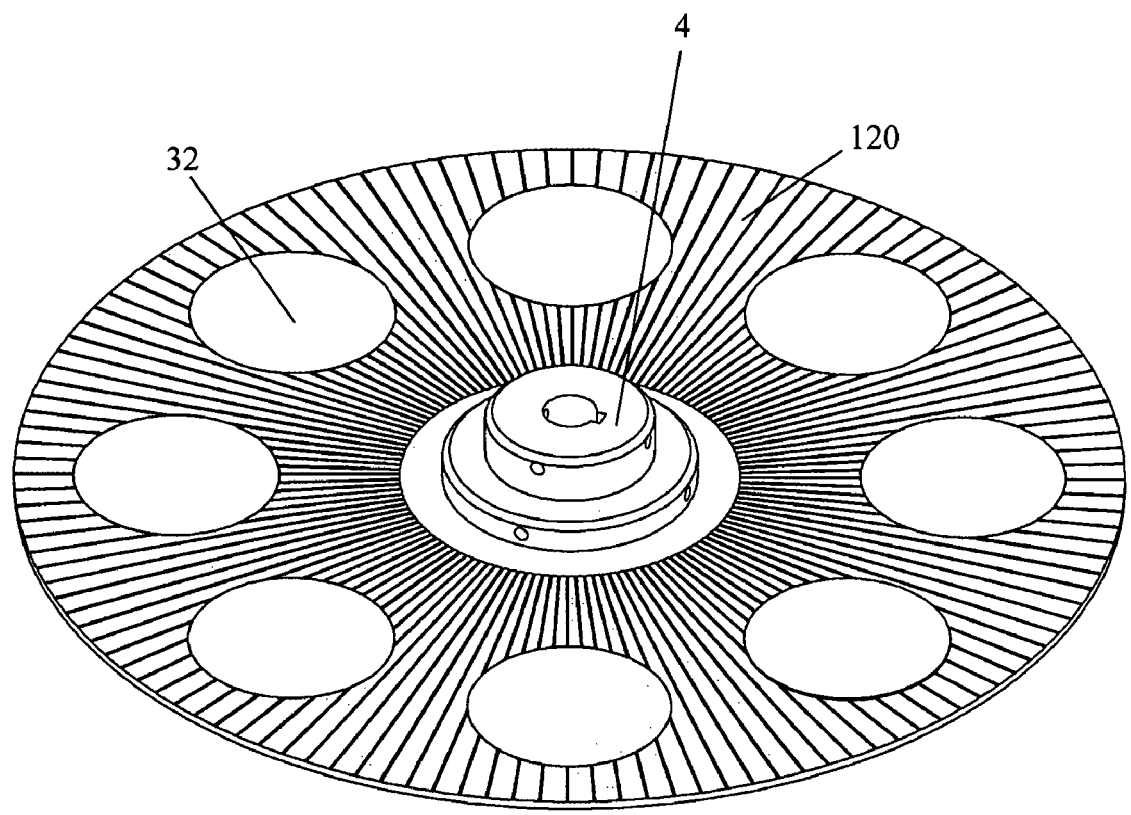
FIGS. 3A and 3B show the lapidary platen cutting side and lapidary platen image side, respectively, of a lapidary platen in accordance with an embodiment of the subject invention.
Figure 3B:
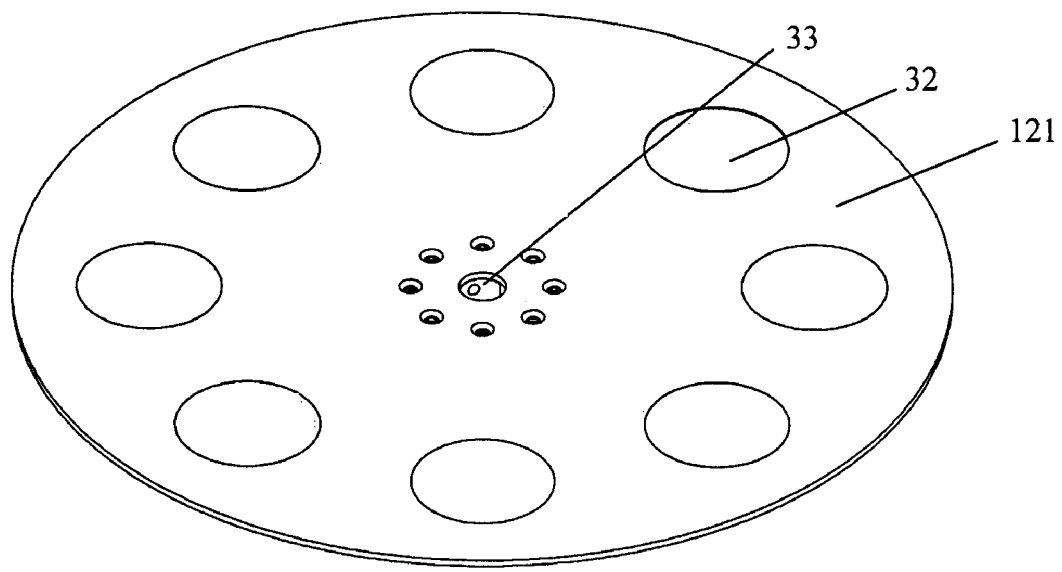
Figure 9A:
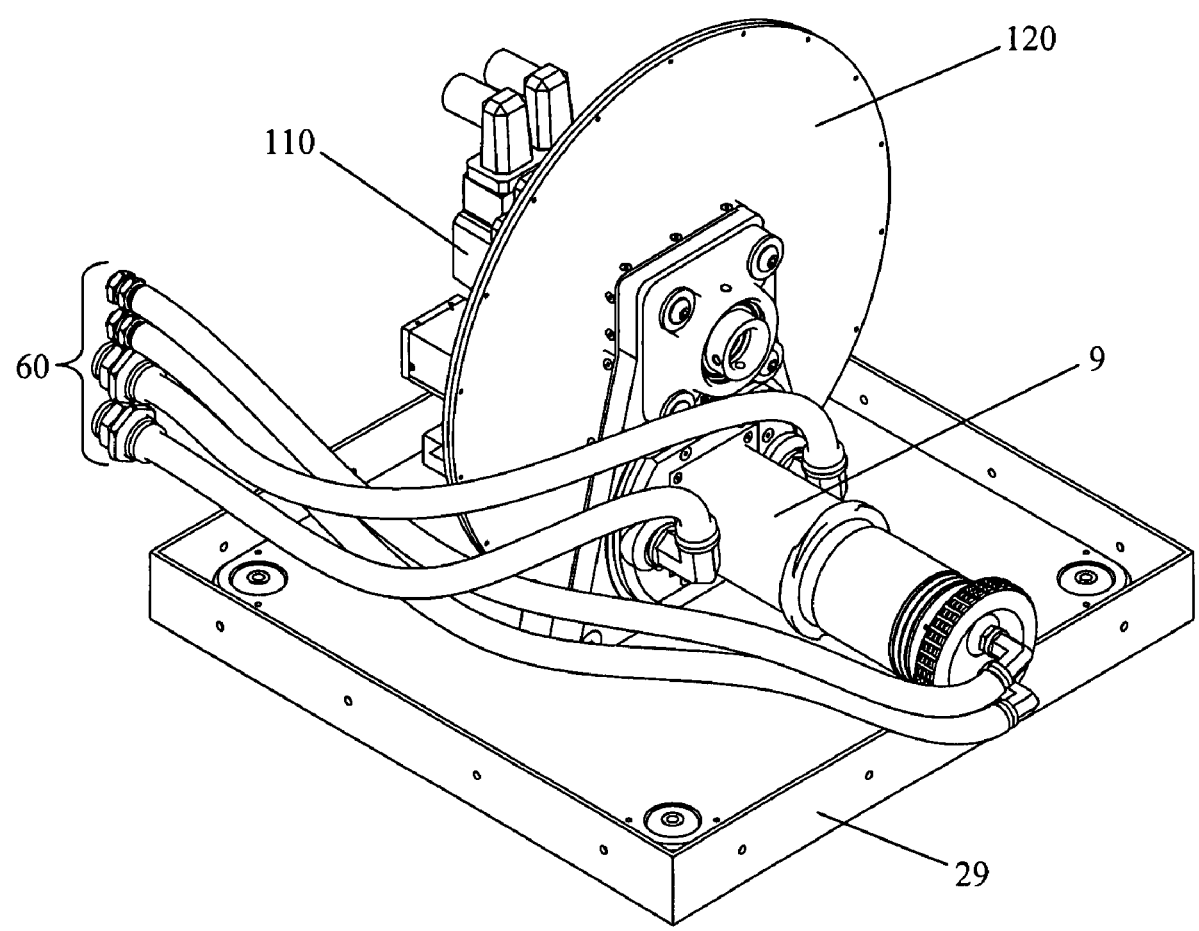
FIGS. 9A and 9B show an embodiment of a 3D lapidary scanner having a servo control, lapidary platen (sample side), sample insert mechanism, and air and fluid ports, servo motor, digital camera, XZ stage, sample z-axis shuttle mechanism, anti-vibration pad and multi-spectral light source, in accordance with the subject invention.

An embodiment of a lapidary wheel platen in accordance with the subject invention is shown in FIGS. 3A and 3B. In an embodiment, the imaging plane can be the lapidary wheel platen 3. The lapidary platen 3 can have a cutting side 120 and an image side 121. FIG. 9A shows a cover 122 that can act as a safety shield and a fluid squeegee and collection method.

In an embodiment, there can be several slots 32 in the lapidary platen wheel that can hold engineered light filters of various optical properties. In an embodiment, the light filters can be secured in the slots 32 by sealant and conical fit. The light filters can provide the ability to capture data of only certain wavelength ranges and/or orientations. In an embodiment, one or more light filters can be clear. In a further embodiment, one or more light filters can be opaque to infrared (IR) frequency light. In a specific embodiment, the filters can be arranged in the form of a standard additive and subtractive color wheel spectrum. In particular, Red, Green, Blue (additive) and Yellow, Cyan, Magenta (subtractive) filters can be used. The additive and subtractive color filters can be adjusted to be able to detect light frequencies that are related to biological luminescent tagents. As an example, the relationship of the color filters can be as follows: red+blue=magenta; red+green=yellow; and green+blue=cyan.

For low cutting rates, the data recorded by each color can be virtually the same. The color filters can provide a versatile spectrum to choose from. In addition, the filters can be various shapes such as 1 cm wide strips for use with flatbed scanners to a clear-glass filter shown in window 32 of FIG. 3A.

In an embodiment, the lapidary wheel platen 3 can be made of hardened tempered opaque material and can have surface qualities on the cutting side 120 that can directly abrade a sample and can incorporate a lapping compound. The lapping compound can be used to create an abrading surface without embedded coatings. In a specific embodiment, the light filters can have embedded diamond coatings of fixed grades. In such an embodiment, the embedded coatings can provide the abrading surface.

The lapping compound, or lubricant/abrasive, can be selected for its optical qualities so as not to interfere with the imaging of each cutting plane. The lapping compound can incorporate engineered abrasives that are minimally damaging to the lapidary wheel, yet which allow light to transmit through. Abrasion properties of the compound can also be selected to maintain a wheel platen in a constant state of high polish throughout its service life. In other words, the system can be self polishing.

In one embodiment, the abradant can be diamond. A diamond abradant can be used for high hardness samples such as some fossils or rock samples. The diamond abradant can be a doubly covalent bonded carbon such as found in varied grade polishing compounds for jewel cutters. The diamond abradant can easily be used for high hardness samples because of its relative hardness of 10 on the Mohs hardness scale. In another embodiment, Corundum ($Al_2O_3$) can be used. With a Mohs hardness of 9, Corundum can provide a very hard substance that is less expensive than a diamond abradant. Corundum is an industrial abrasive available in commercially pure quantities in many grades. It is also by its particle nature an interesting abrasive because when the sharp corners of the abrasive particles break off, the new particles are not rounded smaller bits, but sharper smaller bits that can keep the fluid fresh and can help prevent scouring of the polishing surfaces.

In a further embodiment, the abradant can be incorporated in a ground activated charcoal slurry that is injected continuously in and around the sample. The charcoal slurry can produce an extremely high contrast background. In a specific embodiment, data processors can use compression routines to reduce dataset size for the 3-D model based on the high contrast background, by for example, a factor of 2-5.

In yet another embodiment, Titanium Oxide ($TiO_2$) can be used as an abradant. The $TiO_2$ abradant can be used for most biological samples because of its relative hardness of Mohs 6.2. Because $TiO_2$ can catalyze with many pollutants and render them harmless, it can be used with samples that produce pollutants. $TiO_2$ can produce a white background, which can be easily digitally filtered out of the images.

It is possible that the imaging window 32 would also abrade very slightly over time, but the abrasion rate of the imaging window 32 would be at a rate much less than the abrasion rate of the sample. The window 32 can be simple and cheap to replace. In embodiments, surface characteristics of the lapidary wheel platen windows 32 can be engineered with both optical and abrasive qualities enhanced.

Figure 8:
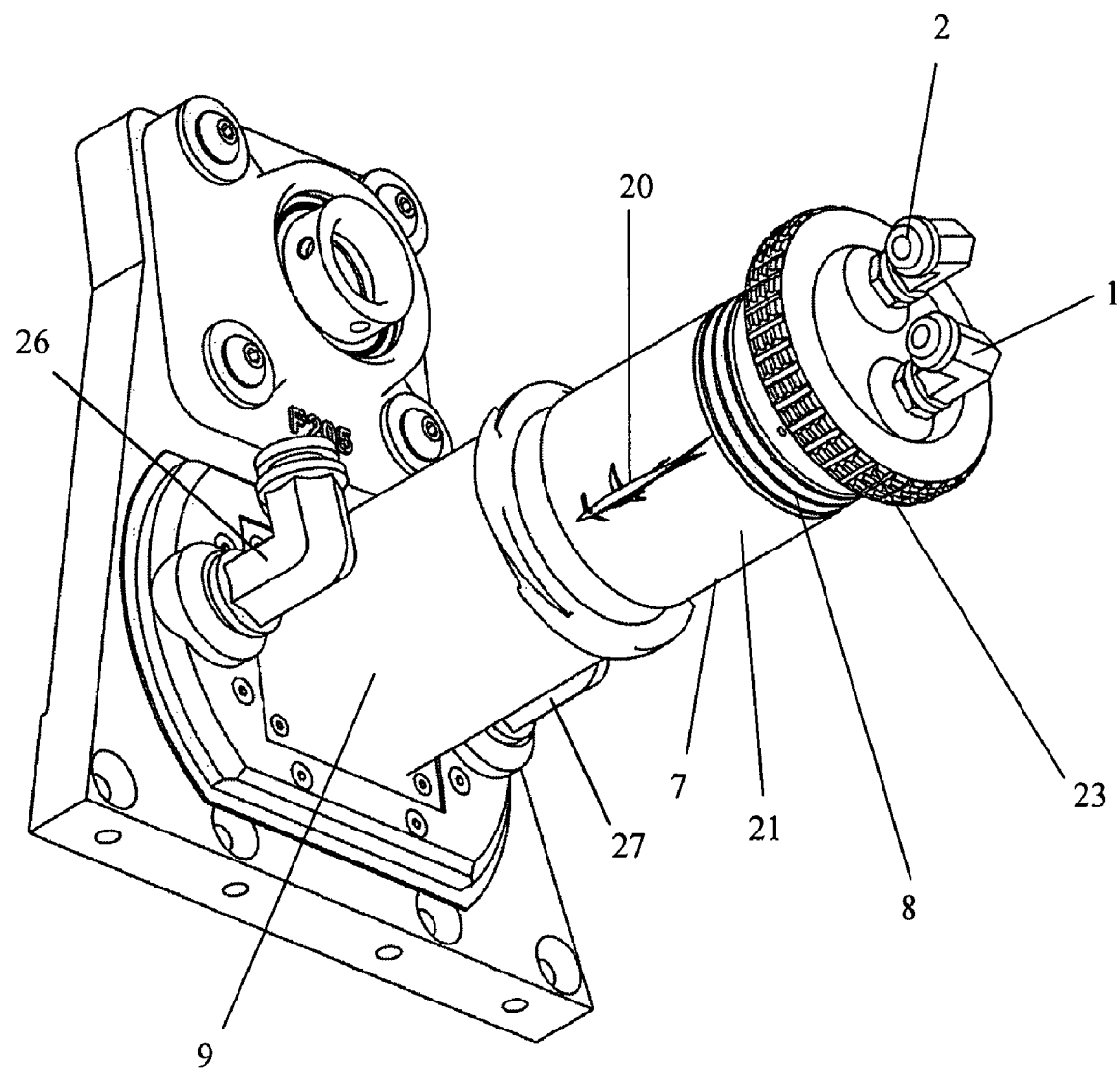
FIG. 8 shows an embodiment of a sample mount according to an embodiment of the present invention, showing a pressure vacuum, fluid in/out and insert sample, tighten cap, use pressure port for z-advance, use vacuum for z-retract.

In operation, the lapping compound can access the platen 3 and cutting surface of the sample through an input port 26 and waste can leave through a waste port 27 of the sample mount as shown in FIG. 8. As illustrated in FIG. 8, a sample can be inserted into the sample feed 9, the cap 23 can be tightened, and vacuum and pressure ports 1 and 2 can be used for z-direction advancement and z-direction retraction, respectively. FIGS. 7A-7D show multiple views of an embodiment of a fluid manifold 13 that can be used to connect the input port 26 and the waste port 27 to the sample mount.

Because lapidary processes polish both a sample and the platen using varied polishing compounds of selected hardness, extremely hard samples, including rock and fossil, can be scanned using the subject method and apparatus.

Figure 4:
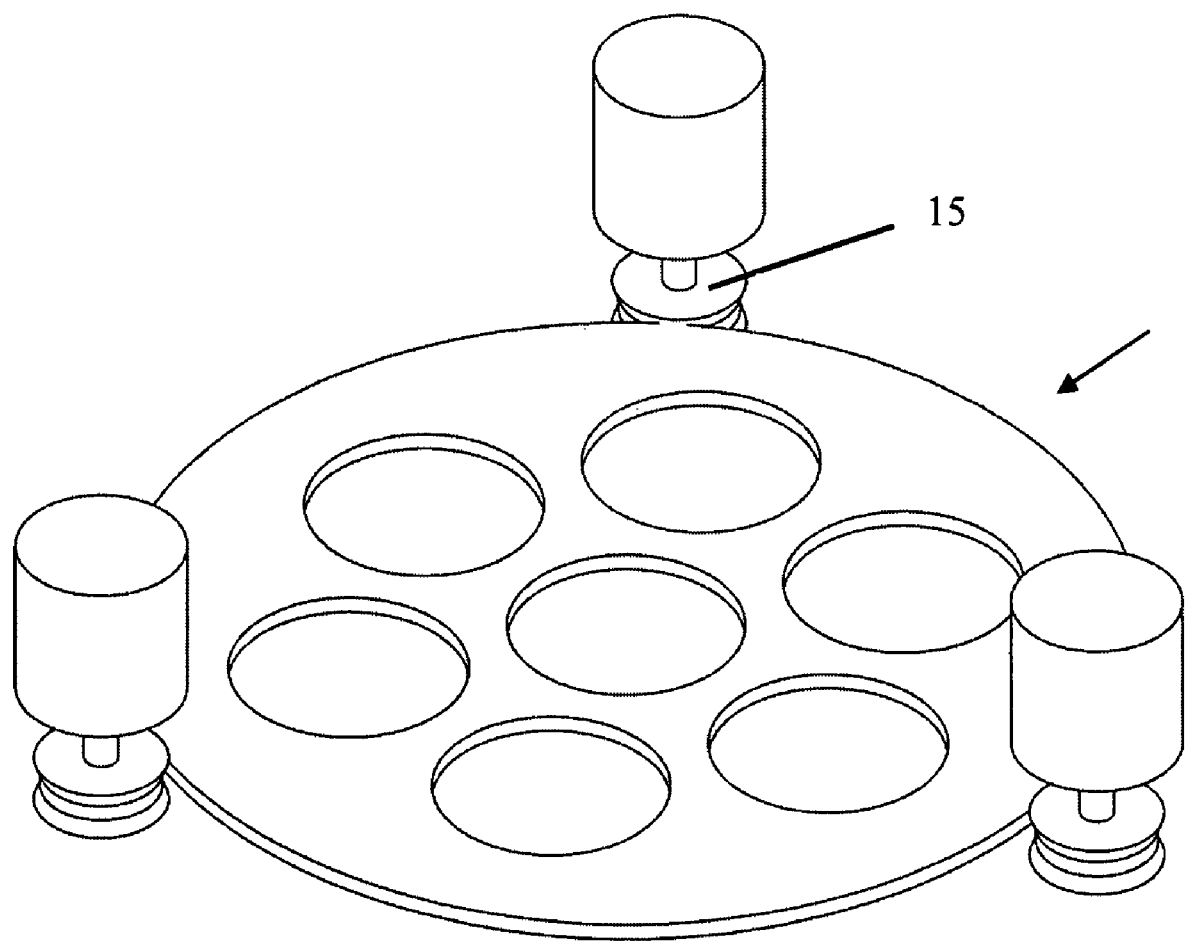
FIG. 4 shows an alternative embodiment of a 3D lapidary scanner annular platen in accordance with the subject invention.
Figure 5A:
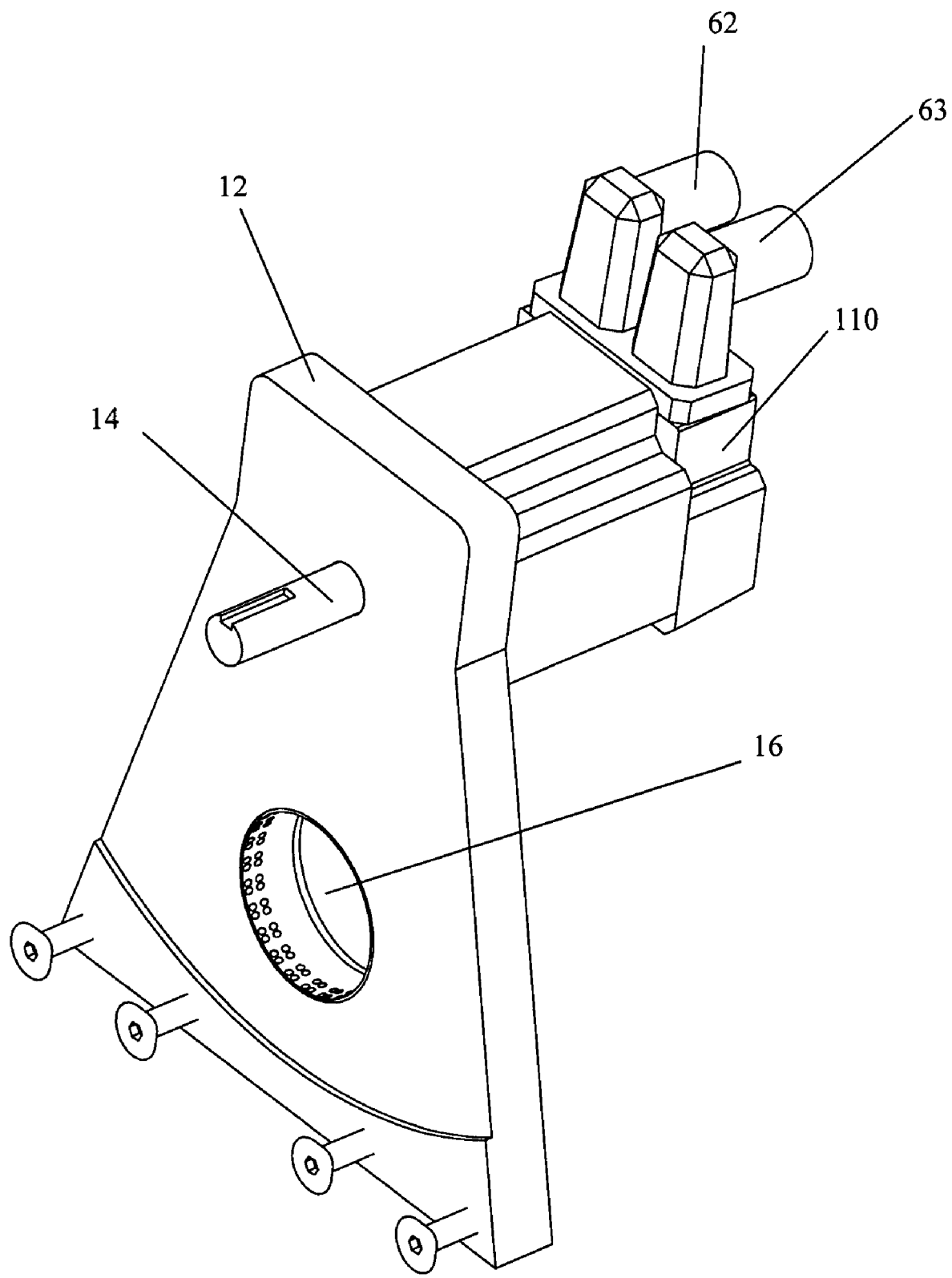
FIGS. 5A and 5B show a front and back view of an embodiment of a motor and image device mount, where
Figure 5B:
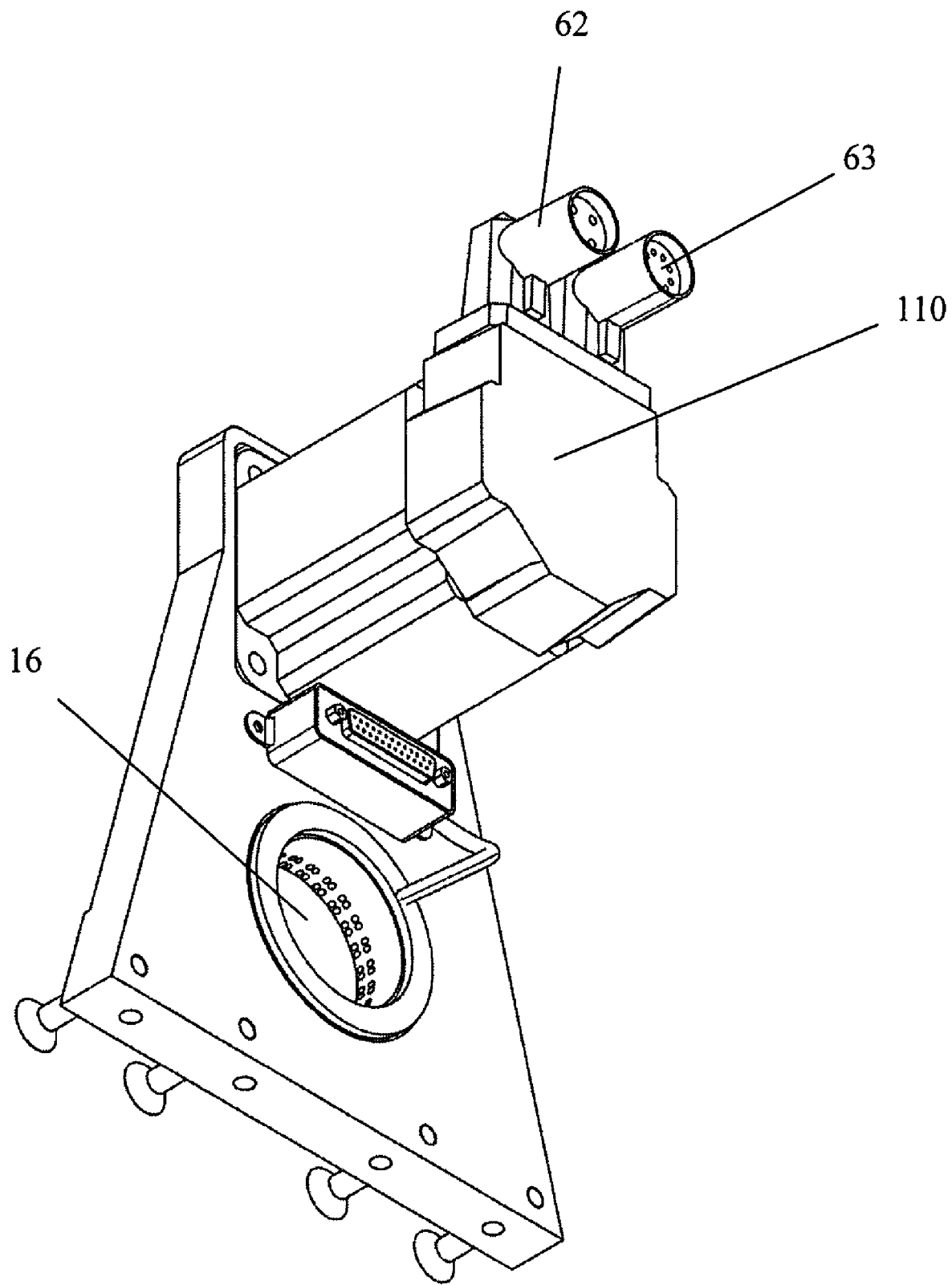
Figure 6A:
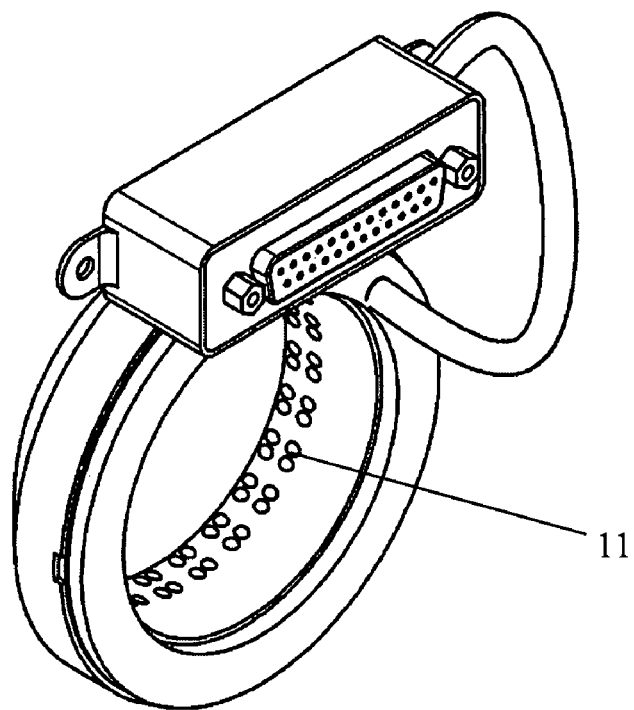
FIGS. 6A-6D show multiple views of an embodiment of a computer controlled multi-spectral light source.
Figure 6B:
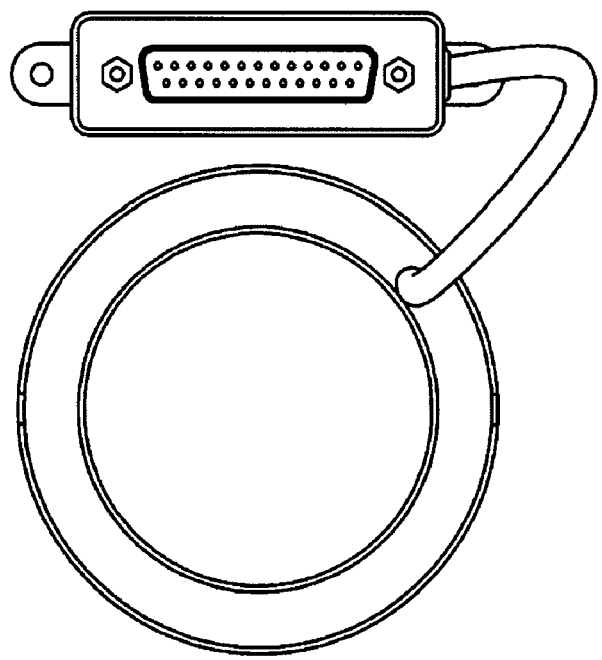
Figure 6C:
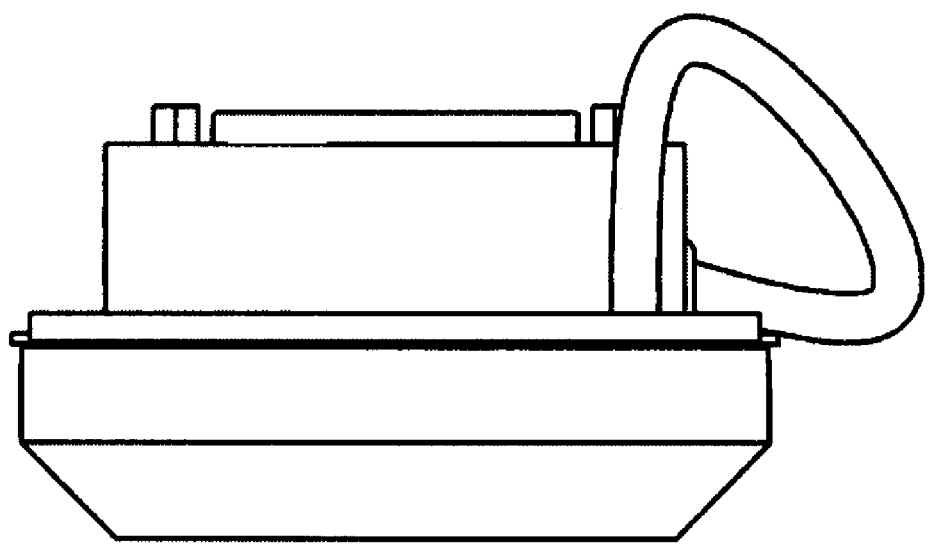
Figure 6D:
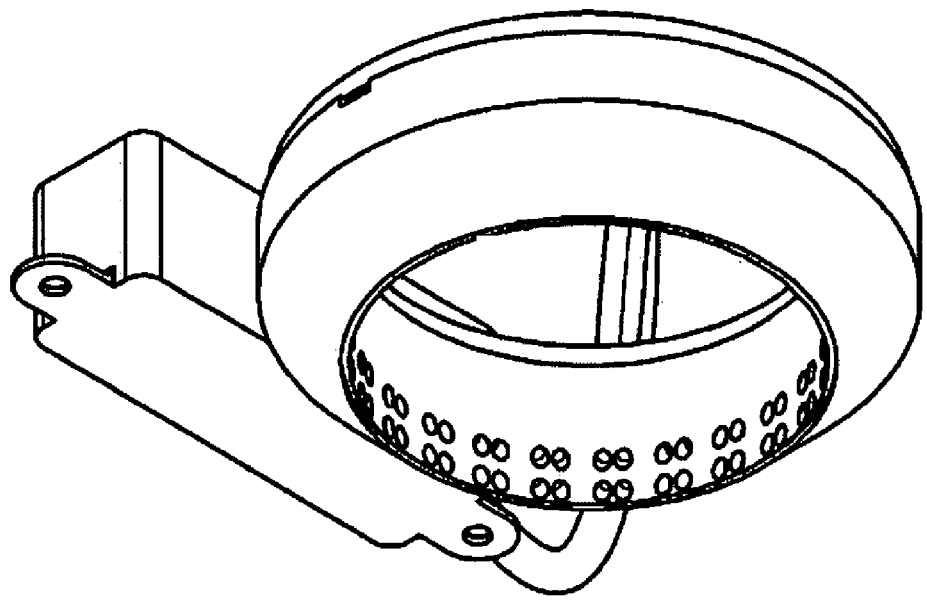
Figure 7A:
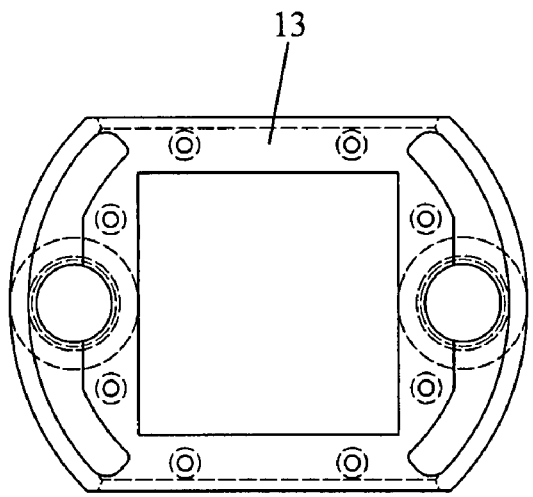
FIGS. 7A-7D show multiple views of an embodiment of a fluid manifold.
Figure 7B:
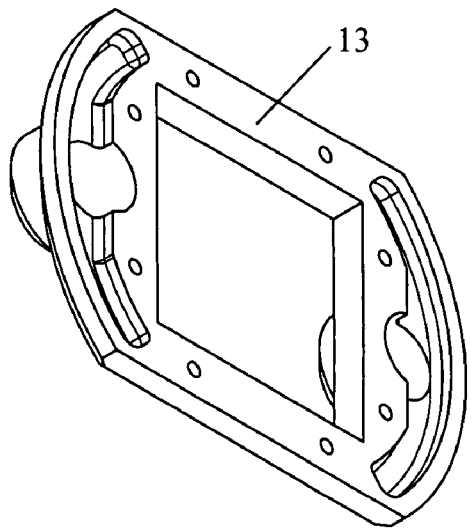
Figure 7C:
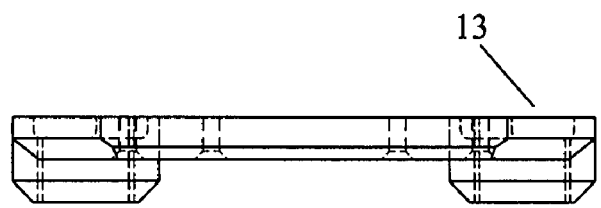
Figure 7D:
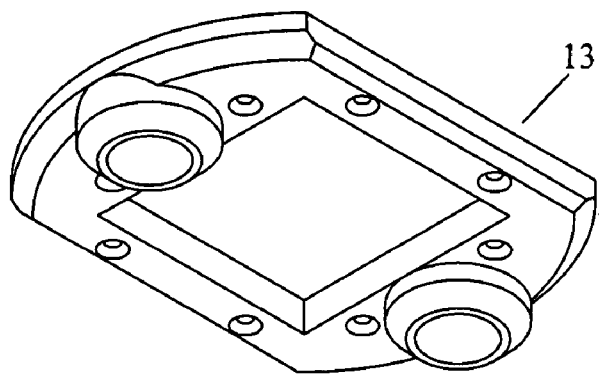

Regarding a driving mechanism, an embodiment, as shown in FIGS. 5A and 5B, can incorporate a motor and a rotating shaft 14 connected to the platen wheel through the wheel's center 33 at the shaft connection 34. In an alternative embodiment, the lapping wheel platen 30, as shown in FIG. 4, can be driven by one or more annular mechanisms 15.

The driving mechanism can be one or more servo motors 6, which can be controlled by a servo motor controller 61. In an embodiment, the servo motors 6 can be encased within a motor mount 110 with control and feedback ports 62 and 63 as shown in FIGS. 5A and 5B.

In various embodiments, the subject apparatus can incorporate microtomes or other cutting instruments. Such embodiments can incorporate more complex instrumentation because an apparatus incorporating microtomes require regular blade replacement and adjustment.

Figure 14A:
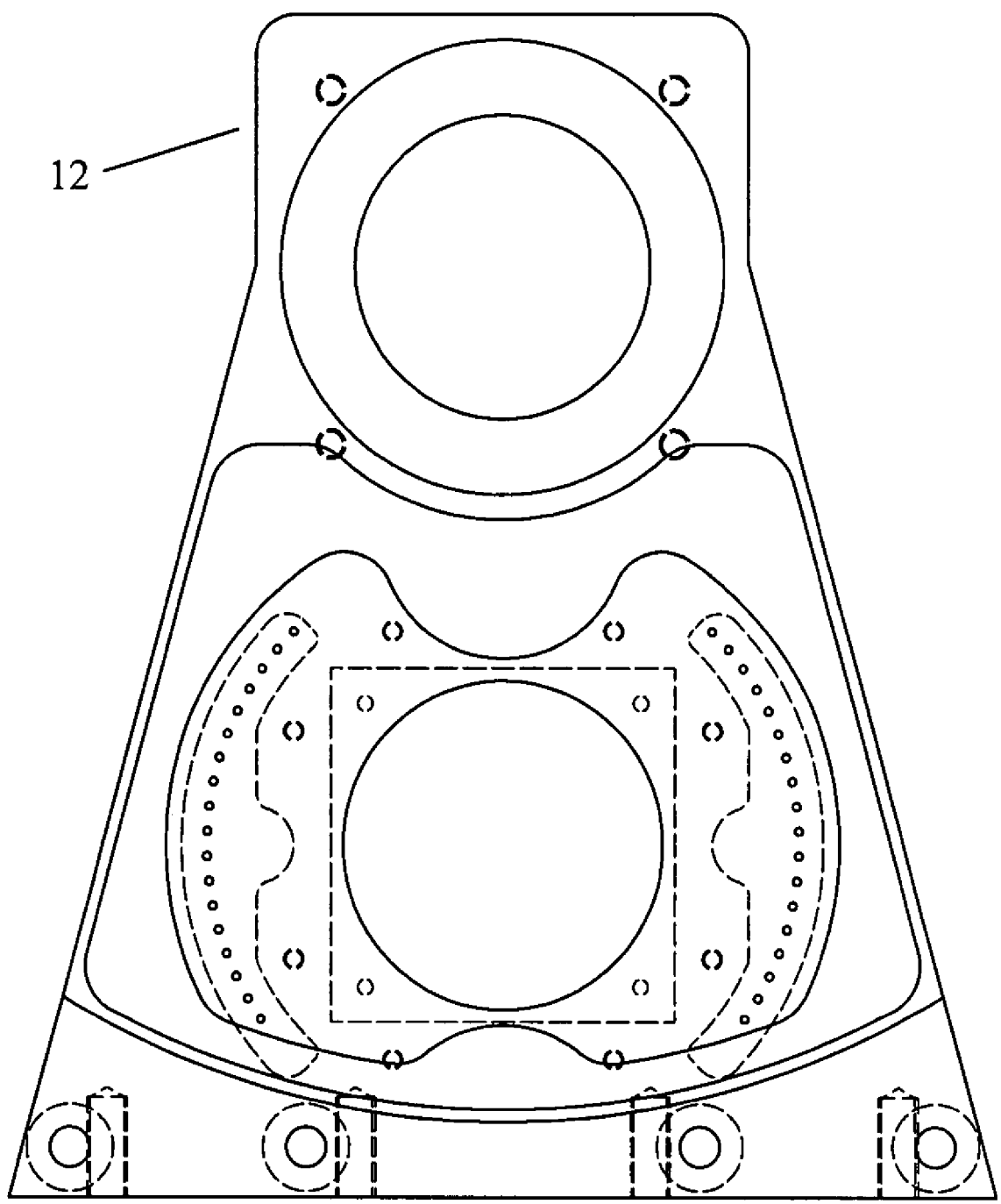
FIGS. 14A and 14B show views of a mount according to an embodiment of the present invention.
Figure 14B:
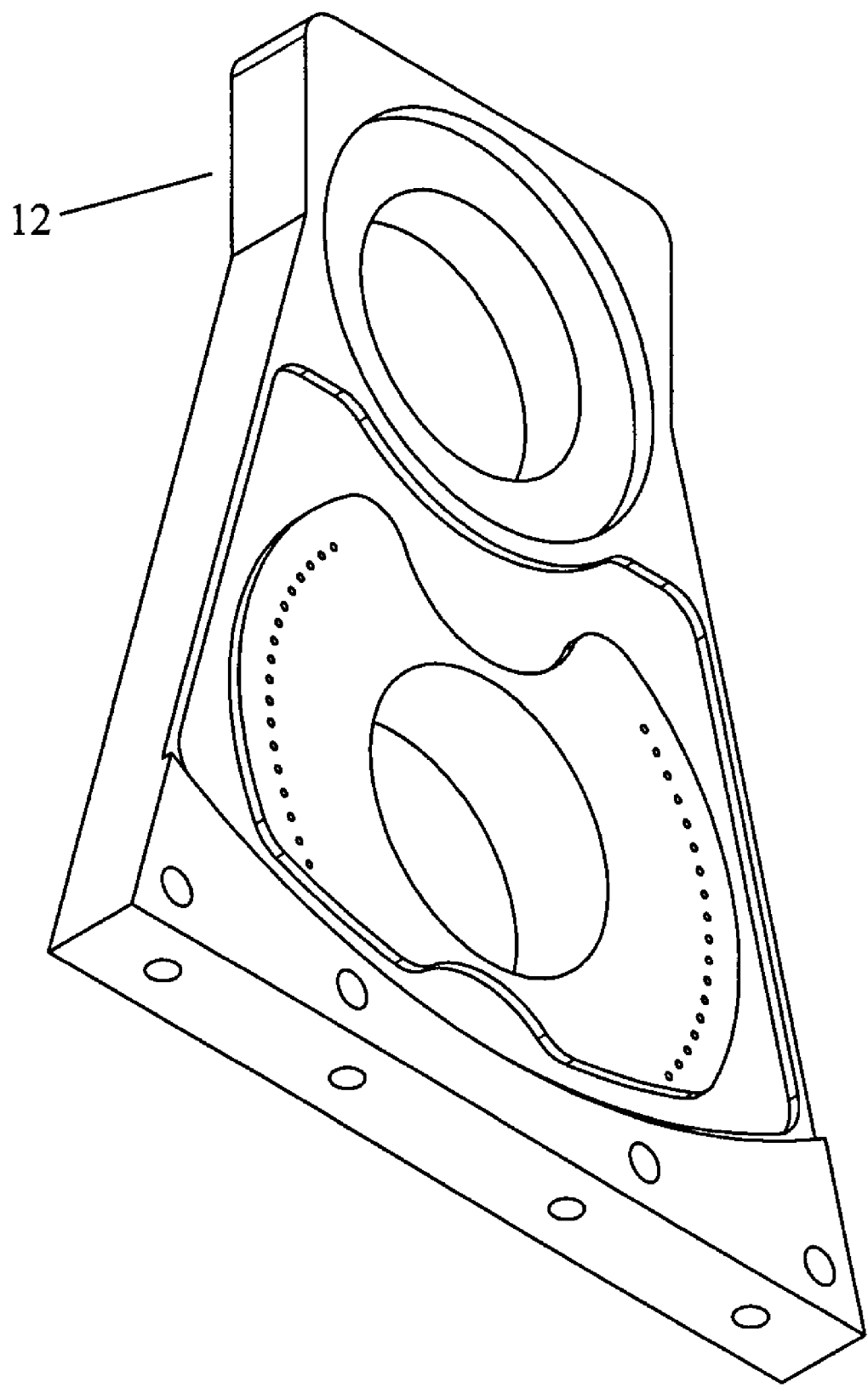

The imaging system can include an image-recording device. The image recording device can access the image plane through the image port 16 of a mount 12 such as shown in FIGS. 5A and 5B. The mount 12 can be formed as illustrated in FIGS. 14A and 14B. In an embodiment, a multispectral light source 11 (detail shown in FIGS. 6A-6D) can be incorporated in the image port. In an embodiment, the image recording device can be a camera. In another embodiment the imaging system can be a system similar to one used in flatbed document scanners or contact photographic emulsion printing. In such embodiments, no lenses are required because the image plane is always registered in the same position. In yet another embodiment, the imaging system can be a video or motion picture imaging system. Such video and other motion picture imaging systems can be used that would allow the continuous recording of the entire process. In further embodiments, digital compression of information can reduce datasets by orders of magnitude. In one embodiment, 3D movies of specimens can be produced by using, for example, time lapse photography. These films can later be digitized to any level of detail required to produce the 3D modeling.

In a further embodiment, combinations of continuous and discrete recording systems can be used such that two distinct data sets can be collected simultaneously. In a specific embodiment, each exposed layer of specimen after an abraded swipe with the lapidary platen is a unique surface that can be analyzed between frames using either a stop motion scanning for detailed high definition images or conventional video imaging, which are known to be 1 to 2 orders of lower resolution for standard video or digital video formats. Because both stop motion scanning and conventional video imaging are good for different results, they can be incorporated into the same device such that two distinct data sets can be collected simultaneously.

For example, a flatbed scanner can collect detailed black and white structural detail. Then, after the scanner moves out of the way, a color camera can snap a high quality color image using selected filters to produce a virtual holographic spectrogram. A Flatbed scanner would take 3-4 times as long if it had to do all 4 colors (CYM-B or RGB-B). The video processors being parallel arrays can be faster.

Figure 9B:
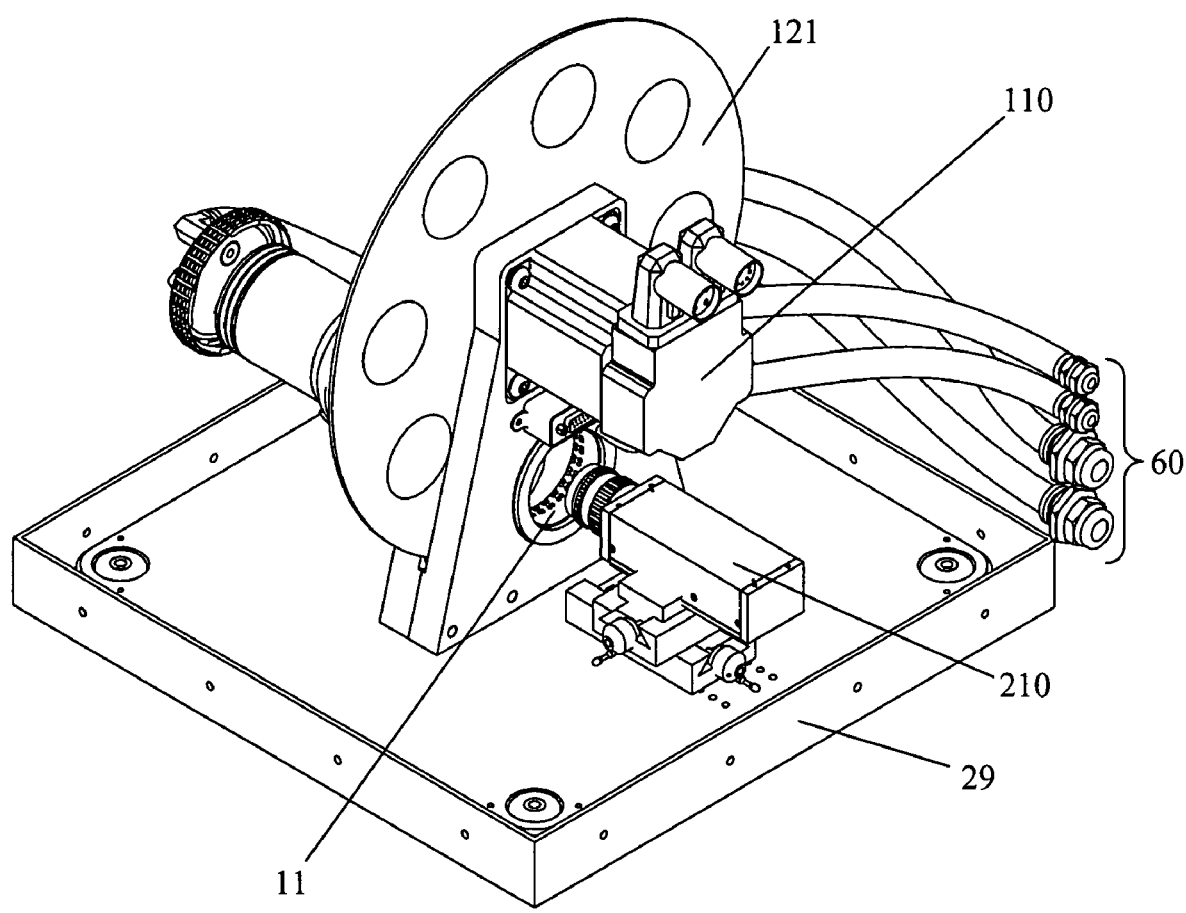

An embodiment incorporating the integrated lapidary, imaging, and control system can be seen in FIGS. 9A and 9B. In an embodiment, the lapidary and image system can be stationed on an anti-vibration pad 29. Fluid and air ports 60 can be connected to an external source. Referring to FIG. 9B, a digital camera 210 can be secured to the anti-vibration pad 29.

Figure 10A:
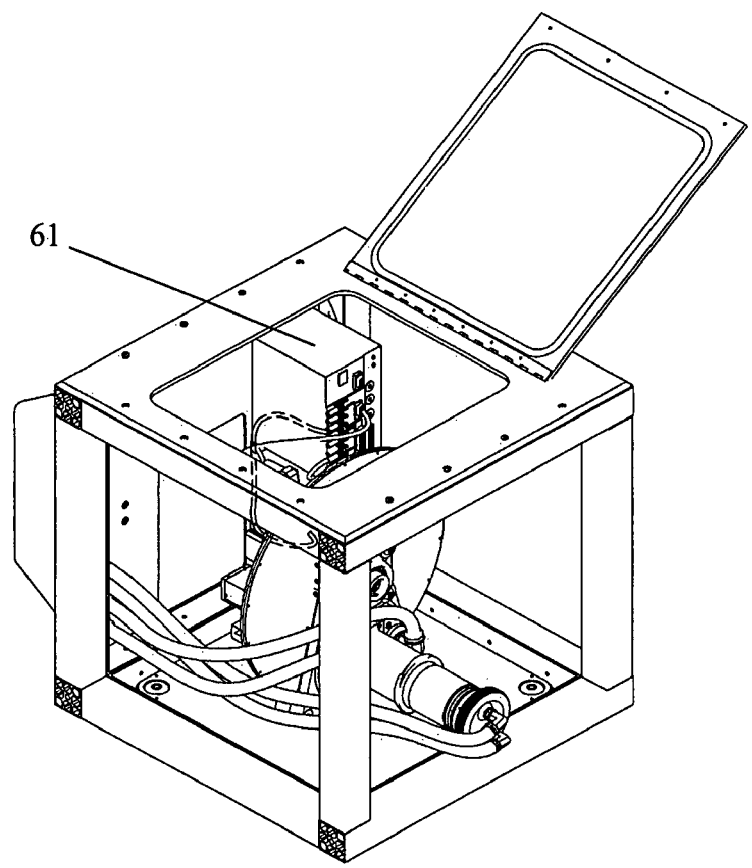
FIGS. 10A and 10B show a front side and a back side of a 3D lapidary scanner in an enclosure, respectively, where the enclosure has clear lexan doors on top, front and sides, and where signals (TYP), fluid ports, camera port, and power are also shown.
Figure 10B:
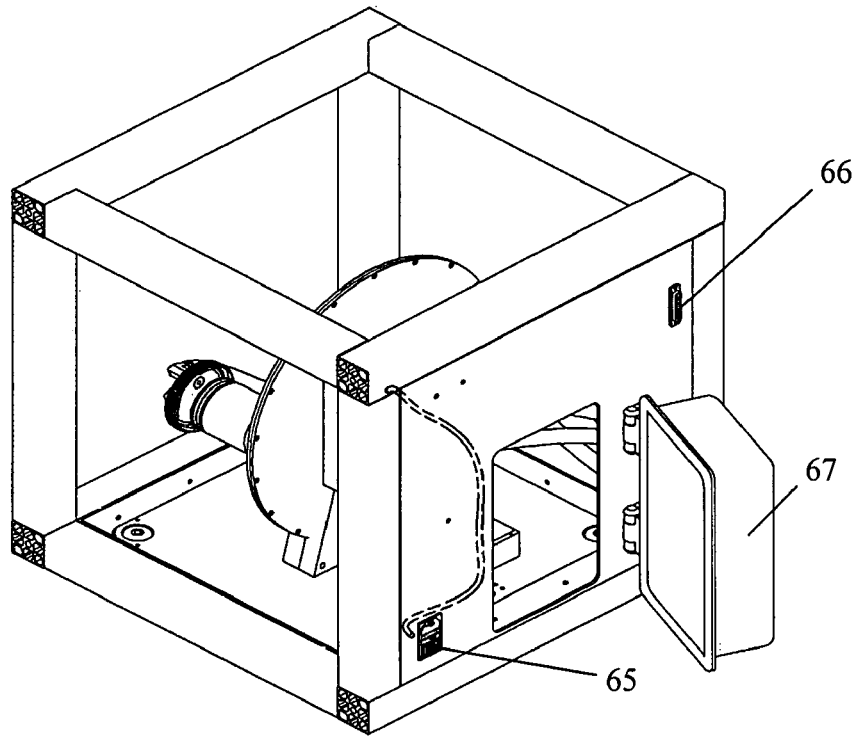
Figure 11:
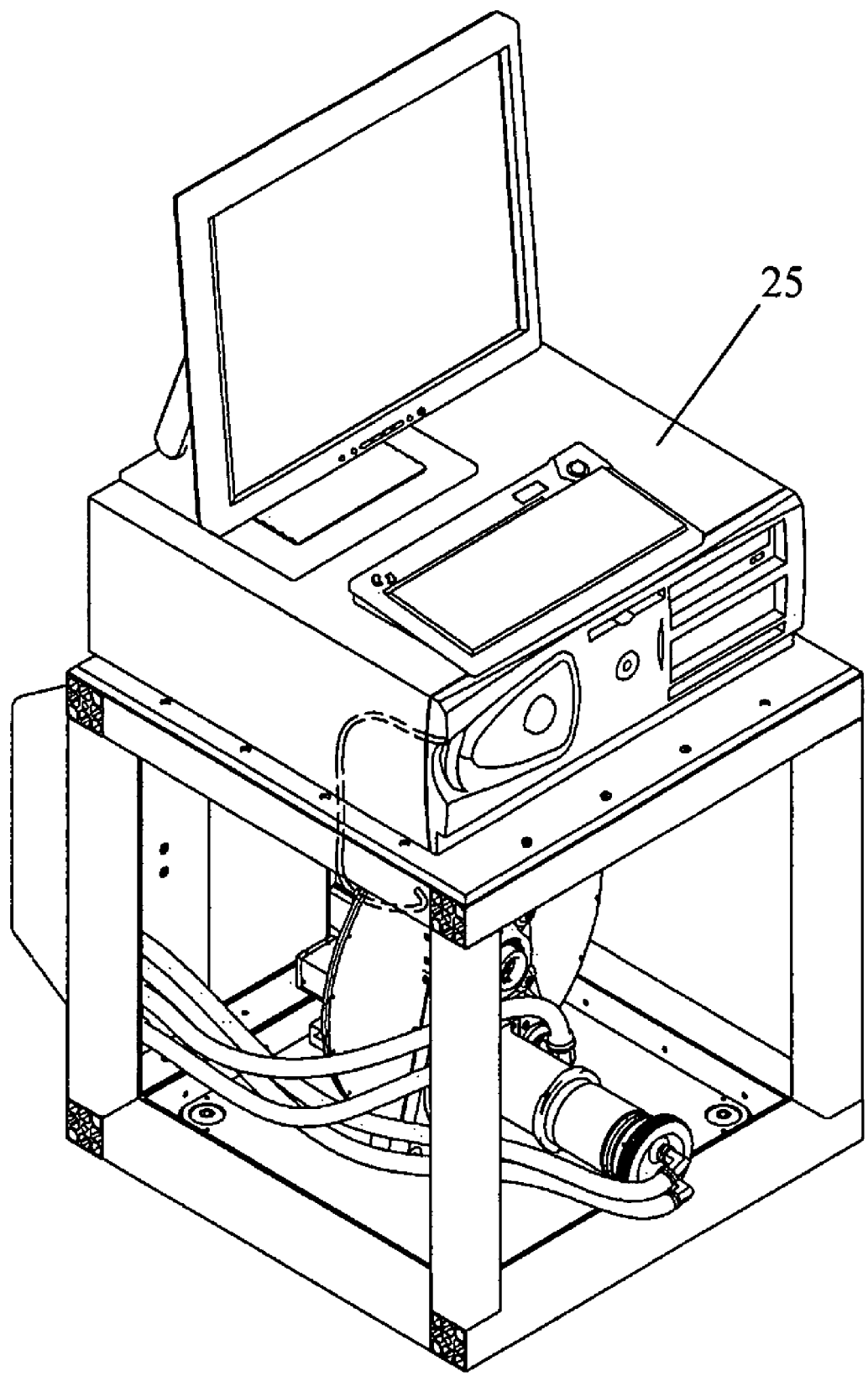
FIG. 11 shows one embodiment of a fully integrated 3D lapidary scanner system with experimental control and data processing, in accordance with the embodiment shown schematically in FIG. 1.

This integrated system can be contained in an enclosure as shown in FIGS. 10A and 10B. The enclosure can include clear Lexan™ doors on top, front, and sides. One side can have connections to the fluid and air ports 60, a power switch 65, and signal ports 66. In one embodiment, a small door 67 can swing to provide access to the imaging system. A controlling unit can be a computer. In an embodiment, the integrated system can be incorporated into an experiment control and data processing workstation 25 as shown in FIG. 11. FIG. 11 shows an embodiment of a fully integrated system in accordance with the subject invention.

Figure 13A:
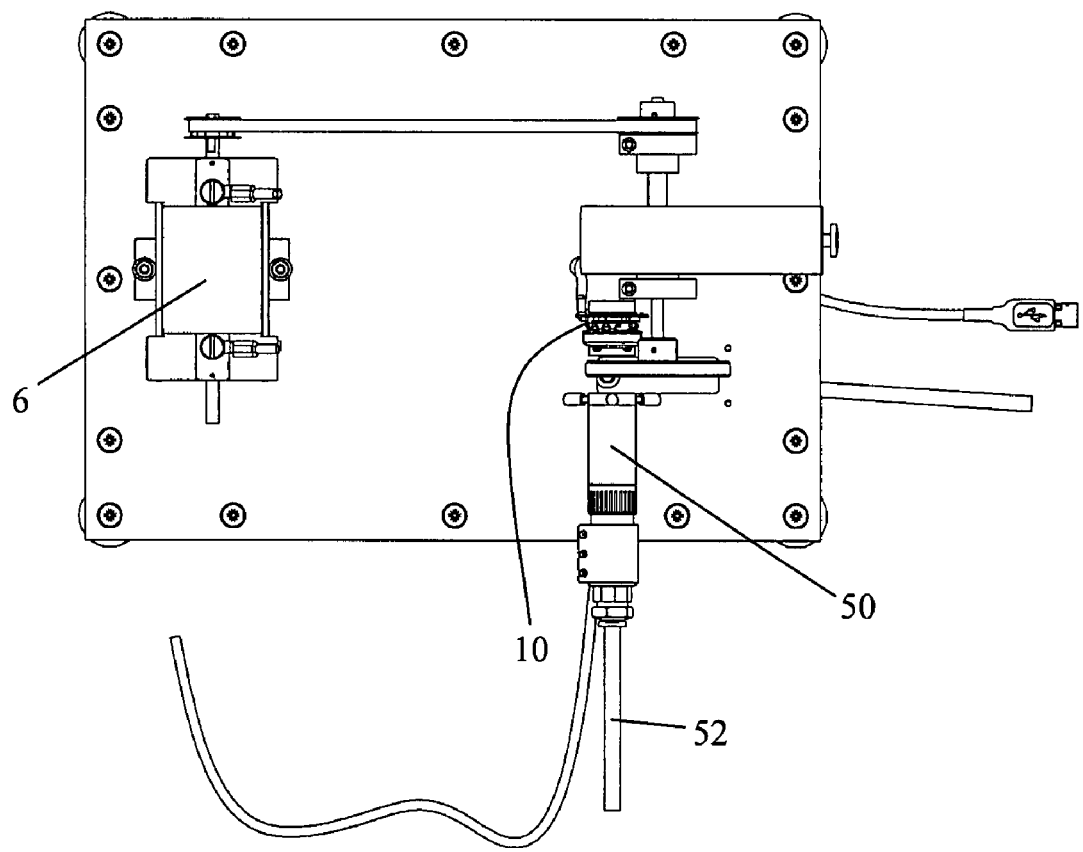
FIGS. 13A and 13B show a top perspective view, and a perspective view of an embodiment of a 3D lapidary scanner incorporating the sample shuttle mechanism shown in FIGS. 12A-12C, respectively.
Figure 13B:
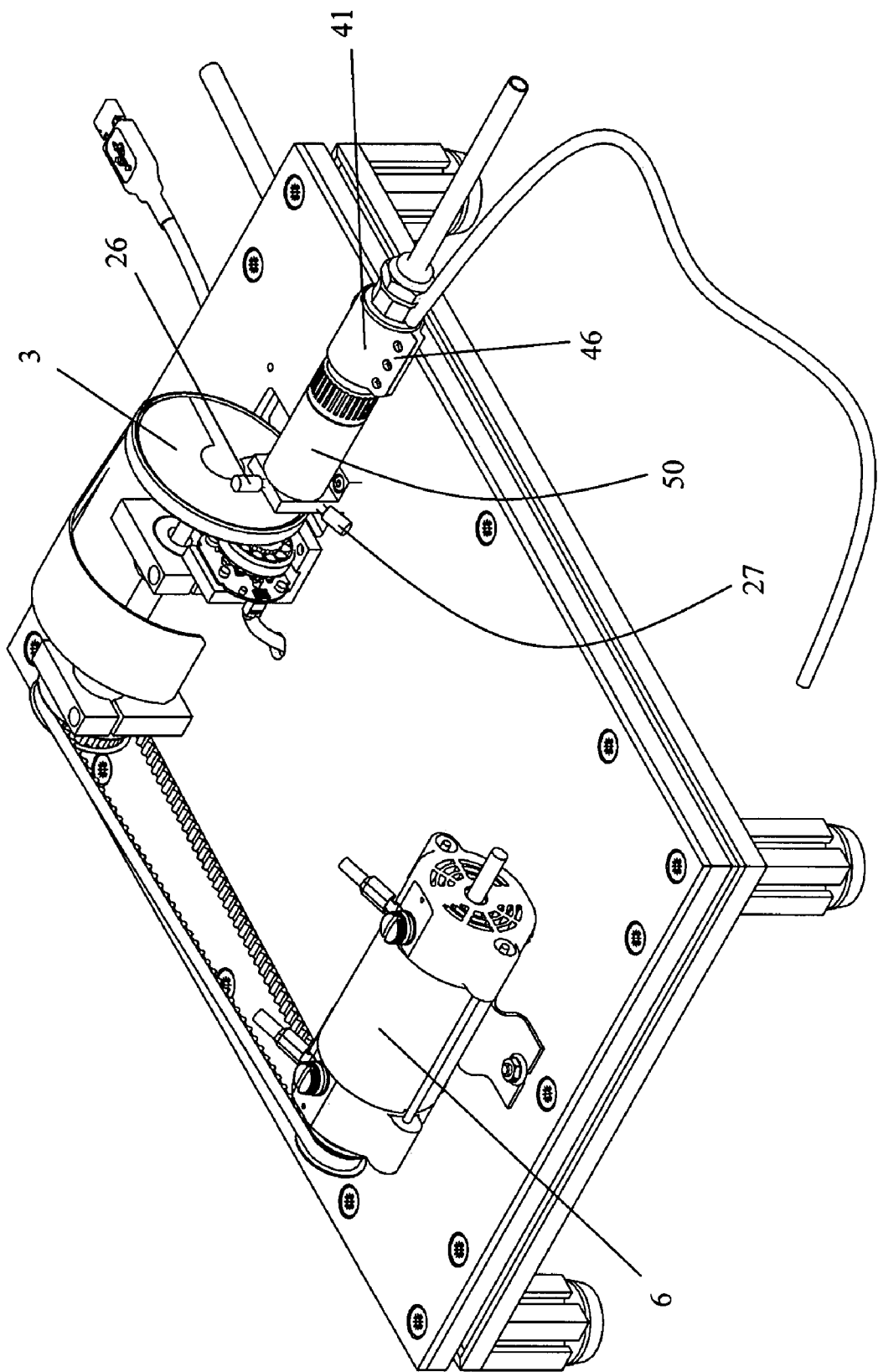

Another embodiment of an integrated system is shown in FIGS. 13A and 13B. FIG. 13A shows a top view of a 3-D scanner prototype according to an embodiment of the present invention, and FIG. 13B shows a perspective view of the 3-D scanner prototype according to an embodiment of the present invention.

The invention can be entirely scaleable from microscopic (1 mm) to macroscopic (10 cm) cross sections.

Embodiments of the subject method and apparatus are more efficient at collecting the data slices and have a lower slice registration error rate compared to prior techniques. Since the cross sections are extremely thin even when compared to a microtome, contamination errors that might have ruined a large slice of hand produced computer assisted model can be simply removed by deleting any entire slice without significant loss or noticeable change to the model. In addition, the subject technique allows such thin layers of the specimen to be removed that the images of the abrading cross-section are sufficient to create acceptable 3D images. The subject technique also includes the ability to maintain the abrading cross-section in the image plane of a camera, simplifying the task of registering the images.

The computer, keyboard and control system 25 can be integrated into a single internet ready system as illustrated in FIG. 17. Much of the optics can be replaced. In addition, in an embodiment binoculars can be used as heads up high density displays. The keyboard itself may be either a touch sensitive screen that can display images or it can be a conventional keypad.

As designed, this version becomes a more practical analytical appliance that can be attractive to many scientific, forensic, medical and semiconductor laboratories interested in anything from geology to nanotechnology.

Figure 15C:
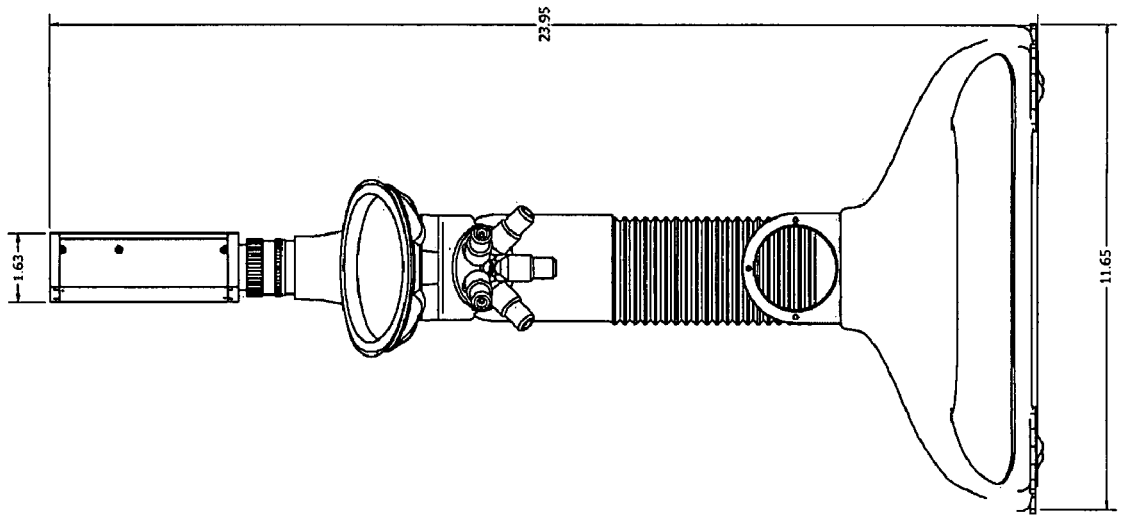
FIGS. 15A-15C show perspective views of an incorporated system according to an embodiment of the present invention.
Figure 15B:
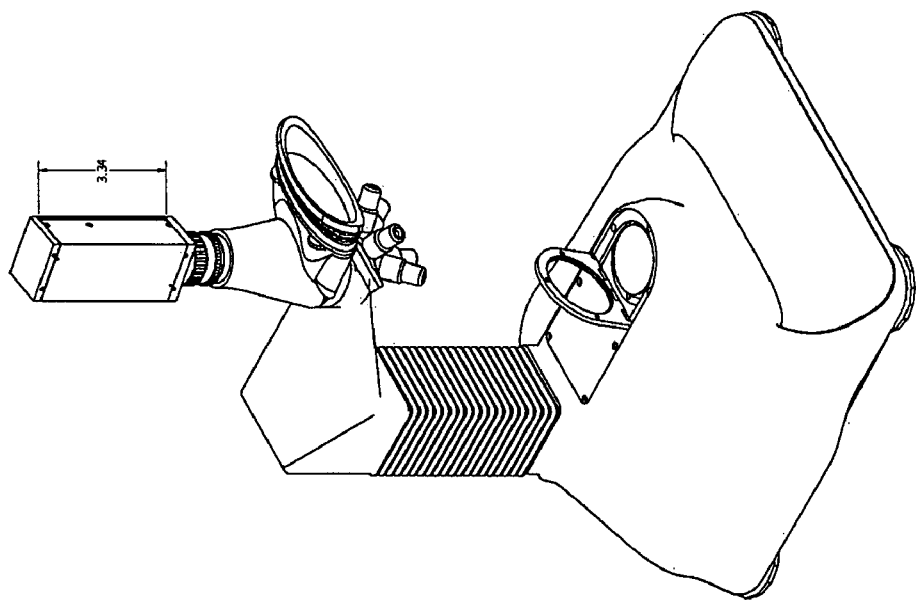
Figure 15A:
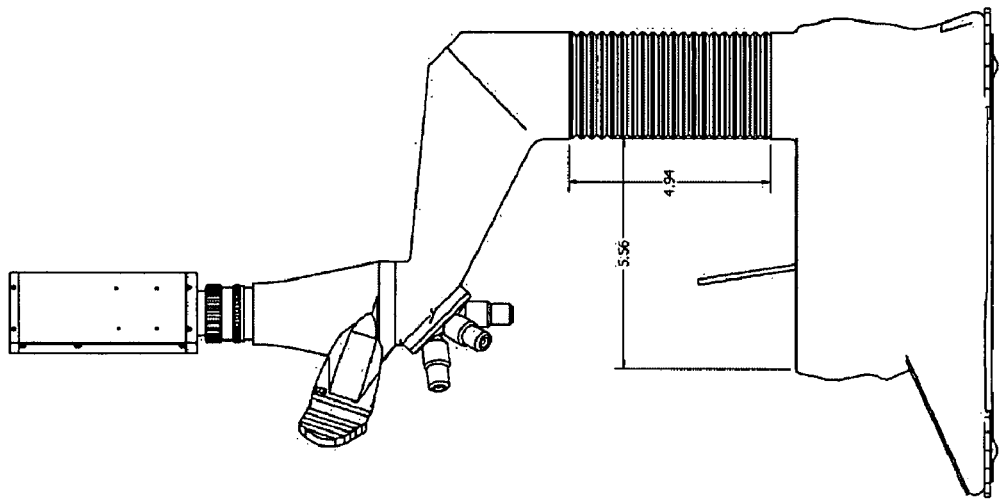
Figure 16:
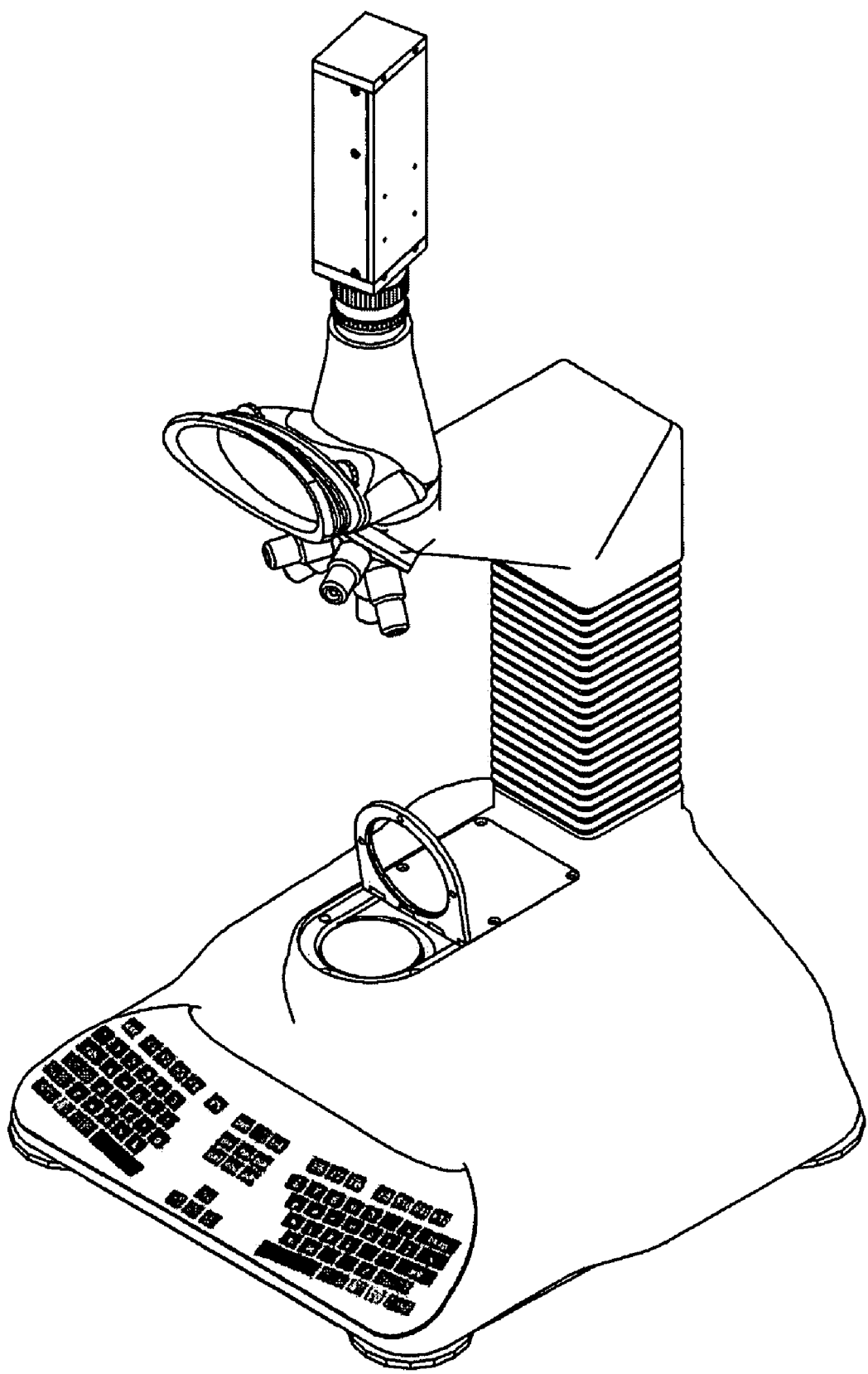
FIG. 16 shows an internet ready system according to an embodiment of the present invention.

Referring to FIGS. 15A-15C, the integrated system can have an incorporated air shuttle advance mechanism with LVDT feedback and diamond coated quartz cutting surfaces that pop out of a collet holder under the lid. As designed, the system can be used as a digital microscope with the simple addition of a stage so it has this versatile feature.

Similar to the embodiments described above, the image plane can be always focused on the abrading plane, and the sample can be stable in the x-y dimension moving along the z axis as it abrades upward exposing layer by layer to be imaged to create highly registered sequential images.

Embodiments of the present invention can incorporate a fully integrated turn key system; collet lapidary disc holder for quick replacement and sample change; fully digital system with normal microscopy ability; multi sensor capability; advanced touch screen keyboard/display system; and built-in computer and storage.

The design shape and form can be provided as illustrated in FIGS. 15A-15C and 16.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

I claim:

1. An apparatus for capturing digitized images of internal structures of specimens, comprising:
    a lapping platen, wherein the lapping platen is capable of removing one or more layers of a specimen from a surface of the specimen to be imaged when in contact with the surface of the specimen to be imaged;
    an image capture device capable of providing digitized images of the surface of the specimen to be imaged in an image plane; and
    a specimen mount, wherein the specimen mount is capable of maintaining the surface of the specimen to be imaged in contact with the lapping platen and in the image plane, wherein the lapping platen comprises embedded filters opaque to infrared frequency light at an abrading plane.

2. An apparatus for capturing digitized images of internal structures of specimens, comprising:
    a lapping platen, wherein the lapping platen is capable of removing one or more layers of a specimen from a surface of the specimen to be imaged when in contact with the surface of the specimen to be imaged;
    an image capture device capable of providing digitized images of the surface of the specimen to be imaged in an image plane; and
    a specimen mount, wherein the specimen mount is capable of maintaining the surface of the specimen to be imaged in contact with the lapping platen and in the image plane, wherein the lapping platen comprises slots for holding at least one engineered light filter.

3. The apparatus according to claim 2, wherein the image capture device comprises a selectable image sensing system capable of detecting images of the surface of the specimen to be imaged in the image plane.

4. The apparatus according to claim 2, wherein the lapping platen comprises a rotary lapping wheel.

5. The apparatus according to claim 2, wherein the lapping platen comprises an orbital sander configuration, an infinite loop belt, or a reciprocating surface.

6. The apparatus according to claim 2, wherein the image recording system comprises a direct digital video capture device and/or a discrete image capture device.

7. The apparatus according to claim 2, further comprising a mechanism to determine depth of a cut or rate of cut into the specimen.

8. The apparatus according to claim 7, wherein the mechanism to determine depth of a cut or rate of cut into the specimen is an estimation using gross measurement of a length of the specimen before the specimen is mounted and model data after processing.

9. The apparatus according to claim 7, wherein the mechanism to determine depth of a cut or rate of cut into the specimen comprises a direct electronic depth sensor.

10. The apparatus according to claim 9, wherein the direct electronic depth sensor comprises a Linear Velocity Displacement Transducer (LVDT) fixed to a specimen shuttle.

11. The apparatus according to claim 7, wherein the mechanism to determine depth of cut or rate of cut into the specimen comprises a mechanical machine tool.

12. The apparatus according to claim 7, wherein the mechanism to determine depth of cut or rate of cut into the specimen comprises disposable wear gauges embedded in a mounting compound around the specimen.

13. The apparatus according to claim 2, further comprising a specimen shuttle capable of advancing and retracting the specimen along the specimen mount, wherein the specimen shuttle comprises:
    a vacuum port and a pressure port, wherein increasing air pressure through the pressure port causes the specimen shuttle to move the specimen toward the lapping platen and reducing air pressure through the vacuum port causes the specimen shuttle to retract the specimen away from the lapping platen.

14. The apparatus according to claim 2, further comprising a control system for coordinating motion of the lapping platen, abrasion of the specimen, and the image recording system.

15. The apparatus according to claim 2, further comprising a driving mechanism to rotate the lapping platen.

16. The apparatus according to claim 2, further comprising an abradant for the lapping platen.

17. The apparatus according to claim 16, wherein the abradant is selected from the group consisting of: diamond, corundum, and titanium oxide.

18. The apparatus according to claim 16, wherein the abradant is selected from the group consisting of: a frozen slurry, an engineered material, nanotechnical particles, and a metal alloyed particle slurry.

19. The apparatus according to claim 2, wherein the specimen mount comprises a collet lapidary disc holder for quick replacement and sample change.

20. The apparatus according to claim 2, further comprising a means for combining the digitized images into a 3-D representation of the specimen.

21. The apparatus according to claim 2, wherein the image capture device comprises a focused plane image capture device.

22. The apparatus according to claim 2, wherein the image capture device comprises a contact image sensing image capture device.

23. The apparatus according to claim 2, wherein the image capture device comprises a full spectrum light detector image capture device.

24. The apparatus according to claim 23, wherein the image capture device comprises one or more of the following: standard photographic emulsion, photomultiplier, charged couple device (CCD), photocell, photo-resistor, complementary metal oxide sensor (CMOS) detector and a hybrid integrated circuit.

25. The apparatus according to claim 2, wherein the image capture device comprises an electromagnetic detector image capture device.

26. The apparatus according to claim 25, wherein the image capture device comprises one or more of the following: antenna, coil, RF energy detector, and triboelectrical effect sensor.

27. The apparatus according to claim 2, wherein the image capture device comprises a physical property detector image capture device.

28. The apparatus according to claim 27, wherein the image capture device comprises one or more of the following: thermocouple, resistance temperature detector, pH-sensor, blackbody thermometer, and Hall effect sensor.

29. The apparatus according to claim 2, wherein the image capture device comprises an HPLC, scanning probe microscope (SPM), scanning electron microscope (SEM), and electron microscope.

30. The apparatus according to claim 2, wherein the image capture device comprises a protein and peptide sensor, lipid sensor, hormone sensor, toxin sensor, and neurotransmitter sensor.

31. The apparatus according to claim 2, further comprising:
a corresponding at least one engineered light filter.

32. The apparatus according to claim 31, wherein one or more of the at least one engineered light filter passes only certain wavelength ranges.

33. A method for capturing digitized images of internal structures of specimens, comprising:
(a) removing one or more layers of a specimen by abrading a surface of a specimen to be imaged via an apparatus, wherein the apparatus comprises:
  (i) a lapping platen, wherein the lapping platen is capable of removing one or more layers of a specimen from a surface of the specimen to be imaged when in contact with the surface of the specimen to be imaged, wherein the lapping platen comprises slots for holding at least one engineered light filter;
  (ii) an image capture device capable of providing digitized images of the surface of the specimen to be imaged in an image plane; and
  (iii) a specimen mount, wherein the specimen mount is capable of maintaining the surface of the specimen to be imaged in contact with the lapping platen and in the image plane;
(b) positioning the specimen via the specimen mount such that the surface of the specimen to be imaged in the image plane;
(c) imaging the surface of the specimen to be imaged via the image capture device to create a digitized image of the surface of the specimen to be imaged; and
(d) repeating (a), (b), and (c) at least once.

34. The method according to claim 33, further comprising combining the digitized images created during (c) into 3-D representations of the specimen.

35. The method according to claim 33, further comprising:
preparing a specimen for mounting to a lapidary system comprising the lapping platen,
wherein preparing the specimen comprises casting the specimen in a rigid compound.

36. The method according to claim 35, wherein casting the specimen in a rigid compound comprises incorporating high contrast mounting materials, dye compounds and/or tagants.

37. The method according to claim 33, wherein positioning the surface of the specimen to be imaged in an image plane comprises holding the specimen in a rigid position in regard to an x-y plane and moving the specimen towards the image plane in the z-direction as each layer of the specimen is removed.

38. The method according to claim 33, wherein positioning the surface of the specimen to be imaged in an image plane comprises holding the specimen rigid as the lapping platen is brought toward the specimen as each layer of the specimen is removed.

39. The method according to claim 33, wherein imaging the surface of the specimen comprises imaging the surface of the specimen through an engineered light filter to detect particular light frequencies.

40. The method according to claim 33, wherein the image capture device comprises a focused plane image capture device.

41. The method according to claim 33, wherein the image capture device comprises a contact image sensing image capture device.

42. The method according to claim 33, wherein the image capture device comprises a full spectrum light detector image capture device.

43. The method according to claim 42, wherein the image capture device comprises one or more of the following: standard photographic emulsions, photomultipliers, charged couple devices (CCD), photocells, photo-resistors, complementary metal oxide sensor (CMOS) detectors and a hybrid integrated circuit.

44. The method according to claim 33, wherein the image capture device comprises an electromagnetic detector image capture device.

45. The method according to claim 44, wherein the image capture device comprises one or more of the following: antenna, coil, and RF energy detectors, and triboelectrical effect sensors.

46. The method according to claim 33, wherein the image capture device comprises a physical property detector image capture device.

47. The method according to claim 46, wherein the image capture device comprises one or more of the following: thermocouple, resistance temperature detector, pH-sensor, blackbody thermometer, and Hall effect sensor.

48. The method according to claim 33, wherein the image capture device comprises an HPLC, scanning probe microscope (SPM), scanning electron microscope (SEM), and electron microscope.

49. The method according to claim 33, wherein the image capture device comprises a protein and peptide sensor, lipid sensor, hormone sensor, toxin sensor, and neurotransmitter sensor.

50. A method for capturing digitized images of internal structures of specimens, comprising:

(a) removing one or more layers of a specimen by abrading a surface of a specimen to be imaged via an apparatus, wherein the apparatus comprises:
  (i) a lapping platen, wherein the lapping platen is capable of removing one or more layers of a specimen from a surface of the specimen to be imaged when in contact with the surface of the specimen to be imaged, wherein the lapping platen comprises embedded filters opaque to infrared frequency light at an abrading plane;
  (ii) an image capture device capable of providing digitized images of the surface of the specimen to be imaged in an image plane; and
  (iii) a specimen mount, wherein the specimen mount is capable of maintaining the surface of the specimen to be imaged in contact with the lapping platen and in the image plane;
(b) positioning the specimen via the specimen mount such that the surface of the specimen to be imaged in the image plane;
(c) imaging the surface of the specimen to be imaged via the image capture device to create a digitized image of the surface of the specimen to be imaged; and
(d) repeating(a), (b), and (c) at least once.

* * * * *

UNITED STATES PATENT AND TRADEMARK OFFICE
CERTIFICATE OF CORRECTION

PATENT NO.        : 7,840,300 B2                                              Page 1 of 1
APPLICATION NO.   : 11/809661
DATED             : November 23, 2010
INVENTOR(S)       : Robert Arthur Harker It is certified that error appears in the above-identified patent and that said Letters Patent is hereby corrected as shown below:

Column 11,
Line 62, "to be imaged in the" should read --to be imaged is in the--.

Column 14,
Line 6, "to be imaged in the" should read --to be imaged is in the--.

Signed and Sealed this
First Day of March, 2011

David J. Kappos
*Director of the United States Patent and Trademark Office*